(12) United States Patent
Wagner et al.

(10) Patent No.: US 8,829,192 B2
(45) Date of Patent: *Sep. 9, 2014

(54) STABILIZATION OF BODY-CARE AND HOUSEHOLD PRODUCTS AGAINST DEGRADATION BY UV RADIATION USING MEROCYANINE DERIVATIVES

(75) Inventors: Barbara Wagner, Lörrach (DE); Oliver Reich, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 1850 days.

This patent is subject to a terminal disclaimer.

(21) Appl. No.: 11/989,164

(22) PCT Filed: Jul. 19, 2006

(86) PCT No.: PCT/EP2006/064388
§ 371 (c)(1),
(2), (4) Date: Jan. 22, 2008

(87) PCT Pub. No.: WO2007/014848
PCT Pub. Date: Feb. 8, 2007

(65) Prior Publication Data
US 2009/0264657 A1 Oct. 22, 2009

(30) Foreign Application Priority Data

Jul. 29, 2005 (EP) .................................... 05107026
Jan. 19, 2006 (EP) .................................... 06100600

(51) Int. Cl.
| | | |
|---|---|---|
| C07D 211/00 | (2006.01) |
| C07C 307/00 | (2006.01) |
| C07C 69/76 | (2006.01) |
| C07D 249/04 | (2006.01) |
| C07C 255/01 | (2006.01) |
| C11D 3/30 | (2006.01) |
| A61K 8/34 | (2006.01) |
| A61K 8/37 | (2006.01) |
| A61K 8/41 | (2006.01) |
| A61K 8/44 | (2006.01) |
| A61K 8/46 | (2006.01) |
| A61K 8/49 | (2006.01) |
| A61Q 1/02 | (2006.01) |
| A61Q 1/04 | (2006.01) |
| A61Q 1/06 | (2006.01) |
| A61Q 1/08 | (2006.01) |
| A61Q 1/10 | (2006.01) |
| A61Q 3/02 | (2006.01) |
| A61Q 13/00 | (2006.01) |
| A61Q 19/00 | (2006.01) |
| C11D 3/00 | (2006.01) |
| C11D 3/28 | (2006.01) |
| C11D 3/34 | (2006.01) |

(52) U.S. Cl.
CPC . *C11D 3/30* (2013.01); *A61K 8/347* (2013.01); *A61K 8/37* (2013.01); *A61K 8/375* (2013.01); *A61K 8/41* (2013.01); *A61K 8/44* (2013.01); *A61K 8/46* (2013.01); *A61K 8/466* (2013.01); *A61K 8/4926* (2013.01); *A61K 8/496* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 3/02* (2013.01); *A61Q 13/00* (2013.01); *A61Q 19/005* (2013.01); *C11D 3/0084* (2013.01); *C11D 3/28* (2013.01); *C11D 3/349* (2013.01)
USPC ............... 546/184; 548/260; 560/12; 560/75; 558/443; 558/453; 568/430; 568/723

(58) Field of Classification Search
USPC ....... 546/184; 548/260; 560/12, 75; 558/443, 558/453; 568/430, 723
See application file for complete search history.

(56) References Cited

U.S. PATENT DOCUMENTS

| | | | |
|---|---|---|---|
| 4,127,646 A | 11/1978 | Snader | |
| 4,749,643 A * | 6/1988 | Ohlschlager et al. | 430/512 |
| 5,806,834 A | 9/1998 | Yoshida | 252/589 |
| 5,945,091 A | 8/1999 | Habeck et al. | 424/59 |
| 6,194,493 B1 | 2/2001 | Stahrfeld et al. | |
| 6,358,496 B1 | 3/2002 | Zink et al. | |
| 6,531,498 B1 | 3/2003 | Eggenweiler et al. | |
| 6,670,382 B2 | 12/2003 | Sato et al. | |
| 6,908,608 B1 * | 6/2005 | Huglin et al. | 424/70.9 |
| 6,919,473 B2 * | 7/2005 | Bonda et al. | 560/6 |
| 7,407,648 B2 * | 8/2008 | Wagner et al. | 424/59 |
| 7,504,528 B2 * | 3/2009 | Wagner et al. | 558/303 |
| 7,510,703 B2 * | 3/2009 | Richard | 424/59 |
| 7,772,242 B2 * | 8/2010 | Wagner et al. | 514/258.1 |
| 7,790,769 B2 * | 9/2010 | Wagner et al. | 514/579 |

(Continued)

FOREIGN PATENT DOCUMENTS

| | | |
|---|---|---|
| DE | 18 09 453 A1 | 6/1970 |
| DE | 199 53 024 A1 | 5/2001 |

(Continued)

OTHER PUBLICATIONS

English Language Abstract of DE 18 09 453 Jun. 1970.

(Continued)

*Primary Examiner* — Samantha Shterengarts
(74) *Attorney, Agent, or Firm* — Shiela A. Loggins

(57) ABSTRACT

Described is the use of specific merocyanine derivatives for protecting body-care and household products from photolytic and oxidative degradation. These compounds perform outstanding UV absorber properties.

27 Claims, No Drawings

(56) References Cited

U.S. PATENT DOCUMENTS

| | | | |
|---|---|---|---|
| 7,893,292 B2 * | 2/2011 | Wagner et al. | 558/303 |
| 2005/0214233 A1 | 9/2005 | Huglin et al. | 424/59 |
| 2005/0255055 A1 | 11/2005 | Wagner et al. | 424/59 |
| 2006/0040836 A1 | 2/2006 | Lupia et al. | 510/130 |
| 2006/0078518 A1 | 4/2006 | Elder et al. | 424/63 |
| 2006/0204457 A1 | 9/2006 | Toda et al. | 424/59 |
| 2007/0079446 A1 | 4/2007 | Lupia et al. | 8/115.51 |
| 2007/0208112 A1 | 9/2007 | Schambony et al. | |
| 2007/0294837 A1 | 12/2007 | Lupia et al. | 8/115.6 |
| 2008/0009550 A1 | 1/2008 | Lupia et al. | 514/788 |

FOREIGN PATENT DOCUMENTS

| | | | | |
|---|---|---|---|---|
| DE | 102 40 863 | A1 | 3/2004 | |
| EP | 0 873 746 | A2 | 10/1998 | |
| EP | 0 900 824 | A1 | 3/1999 | |
| EP | 1 291 343 | A1 | 3/2003 | |
| EP | 1 396 490 | A1 | 3/2004 | |
| JP | 62 036484 | A | 2/1987 | |
| WO | 00/20388 | A1 | 4/2000 | |
| WO | 03/068183 | A1 | 8/2003 | |
| WO | WO 2004/006878 | * | 1/2004 | 544/106 |
| WO | 2005/058269 | A1 | 6/2005 | |
| WO | 2005/080341 | A1 | 9/2005 | |
| WO | 2005/100319 | A1 | 10/2005 | |
| WO | 2006/003094 | | 1/2006 | |
| WO | 2006/016806 | | 2/2006 | |
| WO | 2006/032741 | | 3/2006 | |
| WO | 2007/068707 | A2 | 6/2007 | |
| WO | 2007/071582 | A1 | 6/2007 | |

OTHER PUBLICATIONS

English Language Abstract of EP 0 873 746 (Oct. 1998).
English Language Abstract of JP 62036484 (Feb. 1987).
English Language Abstract of DE 102 40 824 (Apr. 2004).
Toman et al., Journal of Luminescence, vol. 112, No. 104, pp. 386-390 (Apr. 2005).
English Language Abstract of DE 102 40 863 (Mar. 2004).
IP.COM, Jul. 12, 2005 pp. 1-195.
F. Caramia et al., Bollettino Chimico Farmaceutico, vol. 100, Jan. 1, 1961, pp. 93-103.

* cited by examiner

STABILIZATION OF BODY-CARE AND HOUSEHOLD PRODUCTS AGAINST DEGRADATION BY UV RADIATION USING MEROCYANINE DERIVATIVES

The present invention relates to the use of selected light stabilizers for protecting body-care and household products from photolytic and oxidative degradation.

The product trend of recent years towards increasing use of natural substances based on oil and fat in cosmetic formulations and household products also increases the problem of the oxidative degradation of fats and oils, resulting in rancidity. Natural oils or unsaturated fatty acids are hardly ever absent from emulsions. Oxidative changes may sometimes produce reactive metabolites, for example ketones, aldehydes, acids, epoxides and lipoperoxides.

As a result there is on the one hand an undesirable change in the smell of the products and on the other hand substances may be obtained which may alter the skin tolerance. The uncontrolled formation of free radicals on the skin contributes primarily to the initiation and progression of a multitude of pathophysical modulations, for example inflammation, cancerogenesis and the like.

However, oxidative degradation processes are not only found in the case of natural substances based on oil and fat. They are also found in a number of other cosmetic ingredients, such as fragrances and odoriferous substances, vitamins, colourants and the like.

To prevent oxidative degradation processes (photooxidation, autooxidation), so-called anti-oxidants (AO) are therefore used in cosmetic and food products. These antioxidants may be classified into compounds which prevent oxidation (complex formers, reducing agents and the like) and into compounds which interrupt the free radical chain reactions, for example butylated hydroxytoluene (BHT), butylated hydroxyanisol (BHA), gallates, such as propylgallate (PG), or t-butylhydroquinone (TBHQ). However, the latter compounds often do not meet the requirements with respect to pH stability as well as to light and temperature stability.

As a consequence the actives in such containers unadvantageously change their properties due to autoxidative processes. This results for example in a reduction of viscosity and changes in color or smell.

Furthermore, the growing product trend in the recent years has also resulted in an increased use of transparent (glass, PET etc.) containers for cosmetic formulations and household products. Although both glass and ordinary plastics have a certain inherent absorption in the UV-B-range the absorption in the UV-A range is very low.

Various stabilization techniques for clear package products by UV absorption are commonly used and well known. For example broad-band UV light stabilizers of the benzotriazole class enhance product stability and shelf live due to their very good UV-A and UV-B absorption properties compared to other absorbers such as benzophenones which mainly absorb UV-B. The most effective today known stabilizers for preventing or delaying light induced fading of transparent packaged products are e.g. benzotriazole derivativess known under the trade names Ciba TINOGARD HS or Ciba TINOGARD TL.

Surprisingly, it has been found that specific light stabilizers based on merocyanine derivatives perform outstanding UV absorber properties and are therefore suitable for product protection.

Therefore, the present invention relates to the use of merocyanine derivatives of formula

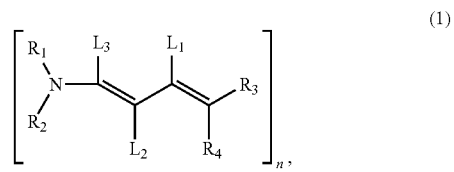

wherein $L_1$, $L_2$ or $L_3$ independently of each other hydrogen; hydroxy; $C_1$-$C_{22}$alkyl; $C_1$-$C_{22}$alkoxy; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl $C_5$-$C_{11}$heteroaralkyl; $C_6$-$C_{20}$aryl; $C_6$-$C_{20}$aryl-$C_1$-$C_5$alkenylene; $C_4$-$C_9$heteroaryl; CN; —(CH$_2$)$_t$—OR$_9$; or COOR$_9$;

$R_4$ is CN; —COR$_7$; —COOR$_7$; —SO$_2$R$_7$; —CONR$_7$R$_8$; $C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_5$-$C_{11}$heteroaralkyl; $C_6$-$C_{20}$aryl; $C_1$-$C_1$alkylcarbonylamino-$C_6$-$C_{20}$aryl; $C_4$-$C_9$heteroaryl;

$R_5$, $R_6$, $R_7$ and $R_8$ are independently of each other hydrogen; $C_1$-$C_{22}$alkyl, $C_2$-$C_{22}$alkenyl, $C_2$-$C_{22}$alkinyl; $C_3$-$C_{12}$cycloalkyl; $C_3$-$C_{12}$cycloalkenyl; $C_7$-$C_{20}$aralkyl; COR$_9$; —(CO)—COO—R$_9$; $C_1$-$C_{20}$heteroalkyl; $C_3$-$C_{12}$cycloheteroalkyl; $C_5$-$C_{11}$heteroaralkyl; $C_6$-$C_{20}$aryl; $C_1$-$C_5$alkoxy-$C_6$-$C_{20}$aryl; —(CH$_2$)$_t$—SO$_3$H; —(CH$_2$)$_t$—(CO)—OR$_9$; —(CH$_2$)$_t$—O—$C_6$-$C_{10}$aryl; —(CH$_2$)$_v$COO—R$_9$; $C_4$-$C_9$heteroaryl; —(CH$_2$)$_u$—SiR$_{15}$R$_{16}$R$_{17}$; or a radical —X-Sil;

$R_9$ is hydrogen; $C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_5$-$C_{11}$heteroaralkyl; $C_6$-$C_{20}$aryl; or $C_4$-$C_9$heteroaryl; or $L_1$ and $L_2$, $L_1$ and $L_3$, $L_2$ and $L_3$, $L_1$ and $R_4$, $L_2$ and $R_4$, $L_1$ and $R_1$, $L_2$ and $R_1$, $L_3$ and $R_1$, $L_3$ and $R_5$, $R_3$ and $R_4$, $R_1$ and $R_2$, $R_7$ and $R_8$, $R_5$ and $R_6$ may be linked together to form 1, 2, 3 or 4 carbocyclic or N, O and/or S-heterocyclic rings, which may be further fused with other aromatic rings and each N in a N-heterocyclic ring may be unsubstituted or substituted by $R_{10}$;

and each alkyl, alkenyl, alkinyl, cycloalkyl or cycloalkylene group may be unsubstituted or substituted by one or more $R_{11}$;

and each aryl, heteroaryl, aralkyl, arylene, heteroarylene or aralkylene may be unsubstituted or substituted by one or more $R_{12}$;

$R_{10}$ is $R_{13}$; COR$_{13}$; COOR$_{13}$; or CONR$_{13}$R$_{14}$;

$R_{11}$ is halogen, OH; NR$_{15}$R$_{16}$; O—R$_{15}$; S—R$_{15}$; O—CO—R$_{15}$; CO—R$_{15}$; oxo; thiono; CN; COOR$_{15}$; CONR$_{15}$R$_{16}$; SO$_2$NR$_{15}$R$_{16}$; SO$_2$R$_{15}$; SO$_3$R$_{15}$; SiR$_{15}$R$_{16}$R$_{17}$; OSiR$_{15}$R$_{16}$R$_{17}$; POR$_{15}$R$_{16}$; or a radical —X-Sil;

$R_{12}$ is $C_1$-$C_{12}$alkylthio; $C_3$-$C_{12}$cycloalkylthio; $C_1$-$C_{12}$alkenylthio; $C_3$-$C_{12}$cycloalkenylthio; $C_1$-$C_{12}$alkoxy; $C_3$-$C_{12}$cycloalkoxy; $C_1$-$C_{12}$alkenyloxy; or $C_3$-$C_{12}$cycloalkenyloxy which may be unsubstituted or substituted by one or more $R_{11}$; halogen; CN; SH; OH; CHO; $R_{18}$; OR$_{18}$; SR$_{18}$; C($R_{18}$)=CR$_{19}$R$_{20}$; O—CO—R$_{19}$; NR$_{18}$R$_{19}$; CONR$_{18}$R$_{19}$; SO$_2$NR$_{18}$R$_{19}$; SO$_2$R$_{18}$; COOR$_{18}$; OCOOR$_{18}$; NR$_{18}$COR$_{19}$; NR$_{19}$COOR$_{20}$; SiR$_{15}$R$_{16}$R$_{17}$; OSiR$_{15}$R$_{16}$R$_{17}$; P(=O)R$_{19}$R$_{20}$; or a radical —X-Sil;

$R_{13}$, $R_{14}$, $R_{15}$, $R_{16}$, $R_{17}$, $R_{18}$, $R_{19}$ and $R_{20}$ independently of each other are hydrogen; $C_1$-$C_{22}$alkyl; $C_3$-$C_{12}$cycloalkyl; $C_2$-$C_{12}$alkenyl; $C_3$-$C_{12}$cycloalkenyl; $C_6$-$C_{14}$aryl; $C_4$-$C_{12}$heteroaryl; $C_7$-$C_{18}$aralkyl; or $C_5$-$C_{16}$heteroaralkyl; or $R_{13}$ and $R_{14}$, $R_{15}$ and $R_{16}$, $R_{16}$ and $R_{17}$ and/or $R_{18}$ and $R_{19}$ may be linked together to form unsubstituted or $C_1$-$C_4$alkyl-substituted pyrrolidine, piperidine, piperazine or morpholine;

X is a linker; and

Sil is a silane-, oligosiloxane or polysiloxane moiety;

t is a number from 0 to 12;

u is a number from 1 to 12;

v is a number from 0 to 12;

if n=1

$R_1$ and $R_2$ independently of each other hydrogen; $C_1$-$C_{22}$alkyl; hydroxy-$C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_6$-$C_{20}$aryl; $C_5$-$C_1$ heteroaralkyl; $C_4$-$C_9$heteroaryl; or a radical of formula

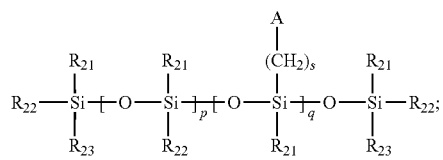

$R_2$, $R_{22}$, $R_{23}$ independently form each other are $C_1$-$C_{22}$alkyl; or $C_1$-$C_{22}$alkoxy;

a is the bond to the linker X;

$R_3$ is CN; $NR_5R_6$; —$COR_5$; —$COOR_5$; —$SO_2R_5$; —$CONR_5R_6$; $C_6$-$C_{20}$aryl; or $C_4$-$C_9$heteroaryl;

p is a number from 0 to 100 q is a number from 1 to 20;

s is a number from 0 to 4;

if n=2

$R_1$ and $R_2$ are each a bivalent radical selected from $C_1$-$C_5$alkylene which may be interrupted by one or more oxygen atoms; or $R_1$ and $R_2$ together with the nitrogen atoms form a six-membered heterocyclic ring; and simultaneously $R_3$ is defined as for n=1; or $R_3$ is a bivalent radical of formula —CO—$V_1$—$C_1$-$C_{12}$alkylene-$W_1$—*, wherein the asterix indicates the bond to the second $R_3$ $V_1$ is —O—; or —$NR_7$—; or the direct bond;

$W_1$ is the linkage to the second $R_3$, wherein $W_1$ is the direct bond; or selected from $C_1$-$C_{12}$alkylene; or phenylene; and $R_1$ and $R_2$ simultaneously are defined as for n=1;

if n=3 one of $R_1$, $R_2$ or $R_3$ is a trivalent radical;

if n=4

$R_1$ or $R_2$ is a radical of formula

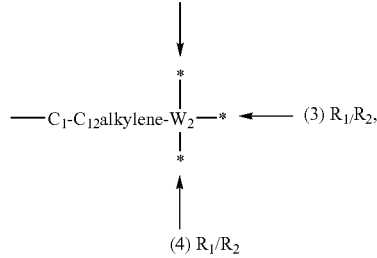

wherein the asterices indicate the bond to the second, third and fourth $R_1/R_2$;

$W_2$ is

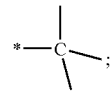

$R_3$ is defined as for n=1; or $R_3$ is a radical of formula

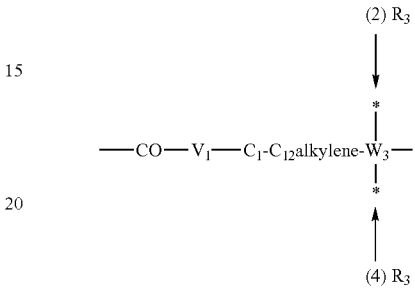

wherein the asterices indicate the bond to the second (2), third (3) and fourth (4) $R_3$; and $W_3$ is

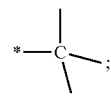

or $R_1$ or $R_2$ is a radical of formula

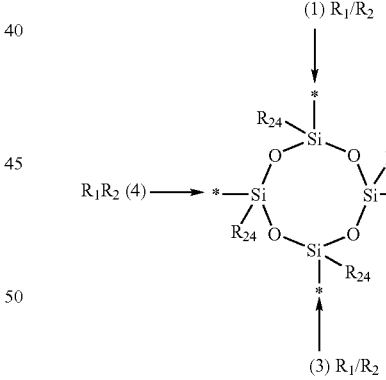

the asterices indicate the bond to the second, third and fourth $R_1/R_2$;

$R_{24}$ is $C_1$-$C_{22}$alkyl; or $C_1$-$C_{22}$alkoxy;

for protecting body-care and household products from photolytic and oxidative degradation.

The term "oligosiloxane" denotes a group of the general formula $Si(R_{21})_m[OSi(R_{22})]_o$; wherein m is 0; 1; or 2, o is 3, 2 or 1; and m and o are 3; or "oligosiloxane" is a group of formula

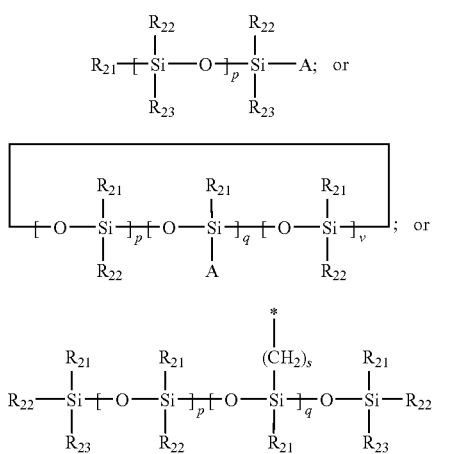

wherein
A is a bond to the linker X;
p is a number from 0 to 10,
q is a number from 1 to 10; and
v is a number from 0 to 1.

The term "polysiloxane" in this context refers to groups of the general formula

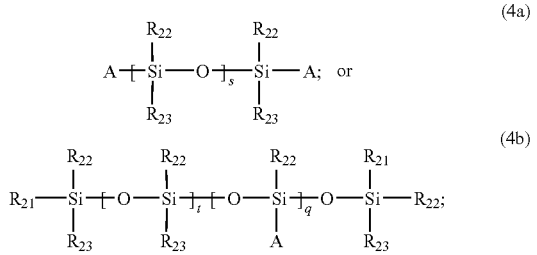

wherein
$R_{21}$, $R_{22}$ and $R_{23}$, independently from each other are $C_1$-$C_{22}$alkyl or $C_1$-$C_{22}$alkoxy;
A is a bond to the linker X;
s is a number from 4 to 250;
t is a number from 5 to 250; and
q is a number from 1 to 30;

Halogen is chloro, bromo, fluoro or iodo, preferably a fluoro, more preferably fluoro alkyl like trifluormethyl, α,α,α-trifluorethyl or perfluorinated alkyl groups like heptafluorpropyl.

Alkyl, cycloalkyl, alkenyl, alkylidene or cycloalkenyl residues can be straight-chain or branched, or also monocyclic or polycyclic.

Alkenyl is for example straight-chain $C_2$-$C_{12}$alkenyl or preferably branched $C_3$-$C_{12}$alkenyl.

$C_1$-$C_{22}$alkyl is for example methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl, oder dodecyl.

$C_3$-$C_{12}$cycloalkyl is for example cyclopropyl, cyclobutyl, cyclopentyl, cyclohexyl, trimethylcyclohexyl, menthyl, thujyl, bornyl, 1-adamantyl or 2-adamantyl.

$C_2$-$C_{12}$alkenyl or $C_3$-$C_{12}$cycloalkenyl refers to unsaturated hydrocarbon residues containing one or multiple double bonds such vinyl, allyl, 2-propen-2-yl, 2-buten-1-yl, 3-buten-1-yl, 1,3-butadiene-2-yl, 2-cyclobutene-1-yl, 2-pentene-1-yl, 3-pentene-2-yl, 2-methyl-1-butene-3-yl, 2-methyl-3-butene-2-yl, 3-methyl-2-butene-1-yl, 1,4-pentadiene-3-yl, 2-cyclopentene-1-yl, 2-cyclohexene-1-yl, 3-cyclohexene-1-yl, 2,4-cyclohexadiene-1-yl, 1-p-menthene-8-yl, 4(10)-thujene-10-yl, 2-norbornene-1-yl, 2,5-norbornadiene-1-yl, 7,7-dimethyl-2,4-norcaradiene-3-yl or different isomers selected from hexenyl, octenyl, nonenyl, decenyl or dodecenyl.

$C_7$-$C_{18}$Aralkyl is for example benzyl, 2-benzyl-2-propyl, β-phenyl-ethyl, 9-fluorenyl, α,α-dimethylbenzyl, ω-phenyl-butyl, ω-phenyl-octyl, ω-phenyl-dodecyl or 3-methyl-5-(1',1',3',3'-tetramethyl-butyl)-benzyl.

The $C_7$-$C_{18}$aralkyl moiety may be unsubstituted or substituted on the alkyl- as well at the aryl-moiety of the aralkyl-group, but preferably is substituted on the aryl-moiety.

($C_1$-$C_6$)-Alkylidene is for example methylene, ethyl-1-ene or propyl-2-ene.

$C_6$-$C_{14}$aryl is for example phenyl, naphthyl, biphenylyl, 2-fluorenyl, phenanthryl, anthracenyl or terphenylyl.

$C_4$-$C_{12}$heteroaryl is for example an unsaturated or aromatic radical with 4n+2 conjugated π-electrons, such as 2-thienyl, 2-furyl, 2-pyridyl, 2-thiazolyl, 2-oxazolyl, 2-imidazolyl, isothiazolyl, triazolyl or any other ringsystem consisting of thiophene-, furan-, pyridine, thiazol, oxazol, imidazol, isothiazol, triazol, pyridine- and phenyl rings, which are unsubstituted or substituted by 1 to 6 ethyl, methyl, ethylene and/or methylene groups, such as benzotriazolyl.

$C_5$-$C_{16}$heteroaralkyl is for example a $C_1$-$C_8$ alkyl moiety which is substituted by a $C_4$-$C_8$heteroaryl group.

Preferably compounds of formula (1) are used, wherein
$L_1$, $L_2$ or $L_3$, independently from each other are hydrogen; hydroxy; $C_1$-$C_5$alkyl, which may be interrupted by one or more oxygen; COOR$_9$; phenyl, which may be substituted by one or more halogen, $C_1$-$C_5$alkyl, $C_1$-$C_5$alkoxy, trifluoroalkyl, $C_2$-$C_5$alkenyl; $C_4$-$C_9$heteroaryl; and
$R_9$ is defined as in claim 1; and
n is 1; and more preferably compounds of formula (1), wherein
$L_1$, $L_2$ and $L_3$, independently from each other are hydrogen, methyl, phenyl; or —COOR$_9$; wherein
$R_9$ is $C_1$-$C_5$alkyl; and
n is 1.

Furthermore, compounds of formula (1) are used, wherein $L_1$ and $L_2$ or $L_1$ and $L_3$ or $L_2$ and $L_3$ together form a bivalent radical selected from

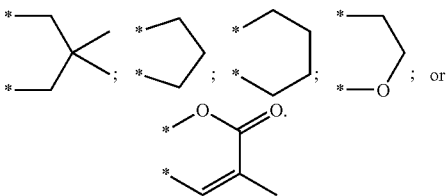

Furthermore, compounds of formula (1) are preferably used, wherein
$R_1$ and $R_2$ independently from each other are $C_1$-$C_{12}$alkyl; hydroxy-$C_1$-$C_{12}$alkyl; phenyl or phenyl-$C_1$-$C_5$alkyl, which may be substituted by one or more $C_1$-$C_5$alkyl, or SO$_3$M; or a radical of formula

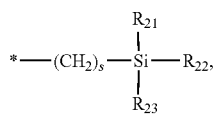

wherein
n is 1; and more preferably compounds of formula (1), wherein
$R_1$ and $R_2$, independently form each other are $C_1$-$C_4$alkyl;
M is hydrogen; or metal ion; and
n is 1.

Furthermore, compounds of formula (1) are preferably used, wherein
$R_1$ and $R_2$ together form a bivalent radical selected from

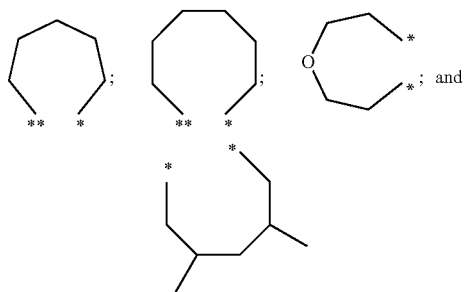

Furthermore, compounds of formula (1) are preferably used, wherein
$R_3$ and $R_4$, independently from each other are CN; $COR_7$; $COOR_7$; $CONR_7R_8$; $SO_2R_7$; wherein
$R_7$ and $R_8$, independently from each other are $C_1$-$C_{22}$alkyl; phenyl; or a radical —X-Sil;
n is 1; and
X and Sil are defined as in claim 1; and more preferably compounds of formula (1), wherein
$R_3$ and $R_4$ together form a carboyclic or heterocyclic biradical selected from

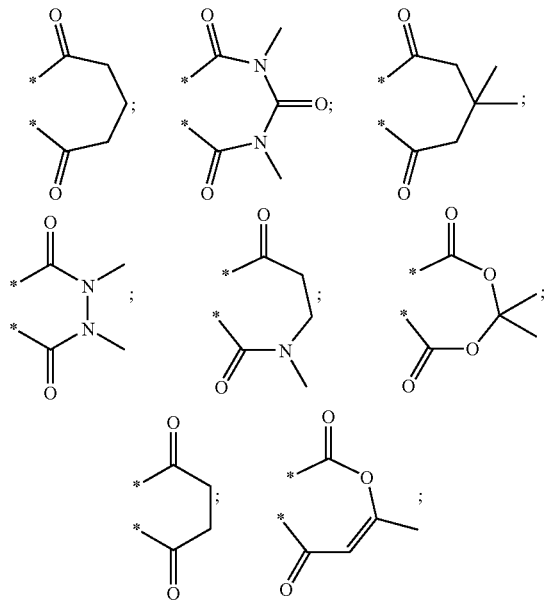

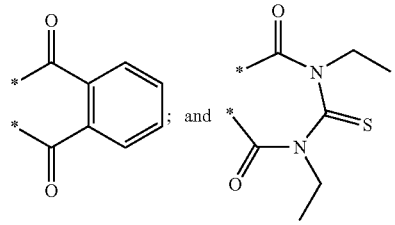

Preferred is also the use of compounds of formula (1), wherein
$R_2$ and $L_3$ form a bivalent radical selected from

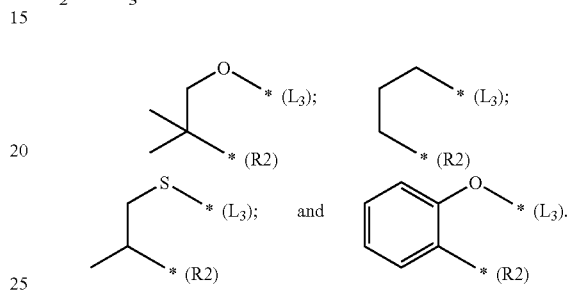

Most preferred is the use of compounds of formula (1), wherein
$L_1$, $L_2$ or $L_3$, independently from each other are hydrogen; hydroxy; $C_1$-$C_5$alkyl, which may be interrupted by one or more oxygen; $COOR_9$; phenyl, which may be substituted by one or more halogen, $C_1$-$C_5$alkyl, $C_1$-$C_5$alkoxy, trifluoroalkyl, $C_2$-$C_5$alkenyl; $C_4$-$C_9$heteroaryl; or
$L_1$ and $L_2$ or $L_1$ and $L_3$ or $L_2$ and $L_3$ together form a bivalent radical selected from

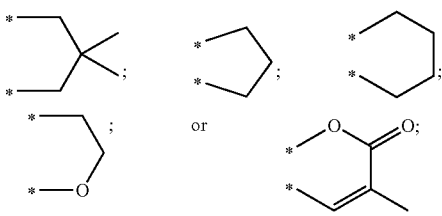

$R_1$ and $R_2$ independently from each other are $C_1$-$C_{12}$alkyl; hydroxy-$C_1$-$C_{12}$alkyl; phenyl or phenyl-$C_1$-$C_5$alkyl, which may be substituted by one or more $C_1$-$C_5$alkyl, or $SO_3M$; or a radical of formula

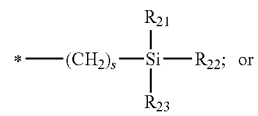

$R_1$ and $R_2$ together form a bivalent radical selected from

-continued

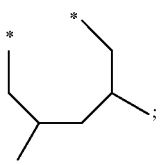

$R_3$ and $R_4$, independently from each other are CN; $COR_7$; $COOR_7$; $CONR_7R_8$; $SO_2R_7$;

$R_7$ and $R_8$, independently from each other are $C_1$-$C_{22}$alkyl; phenyl; or a radical —X-Sil; or $R_3$ and $R_4$ together form a carboyclic or heterocyclic biradical selected from

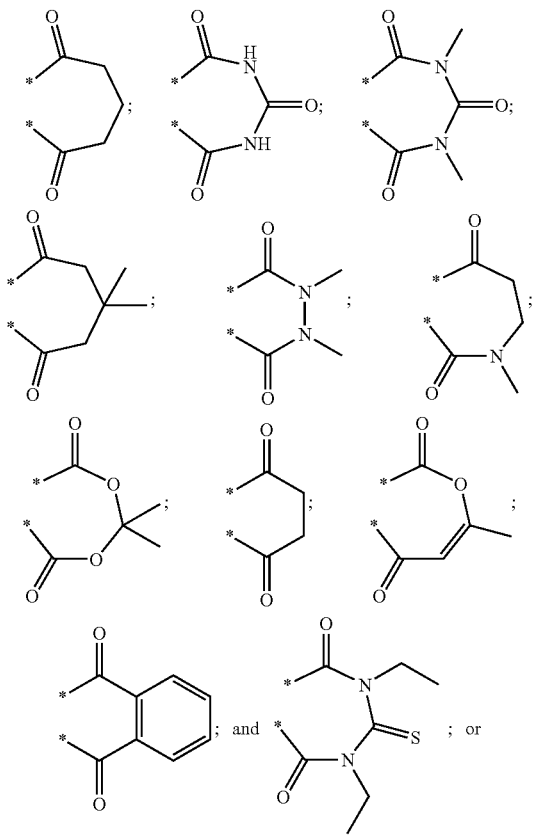

$R_2$ and $L_3$ form a bivalent radical selected from

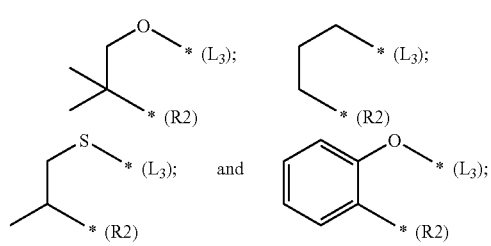

and $R_9$, $R_{21}$, $R_{22}$, $R_{23}$, X and Sil are Defined as in claim 1.

Furthermore, compounds of formula (1) are preferred, wherein the stabilizers correspond to formula

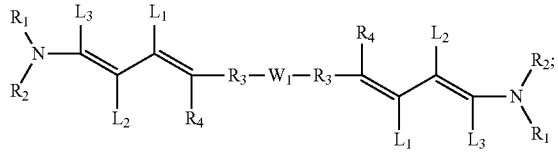

(2a)

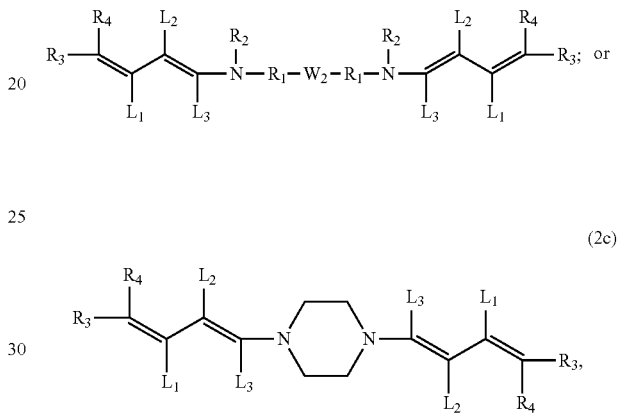

(2b)

(2c)

wherein $R_1$, $R_2$, $R_3$, $R_4$, $L_1$, $L_2$, $L_3$, $W_1$ and $W_2$ are defined as in formula (1).

Preferably compounds of formula (2a) are used, wherein $R_3$ is a radical of formula —CO—$V_1$—$C_1$-$C_{12}$alkylene-**, wherein $V_1$ is —O—; or —NH—;

$W_1$ is the direct bond; $C_1$-$C_4$alkylene; or phenylene;

$R_1$ and $R_2$, independently from each other are $C_1$-$C_{12}$alkyl;

$L_1$, $L_2$ and $L_3$ independently form each other are hydrogen; or $C_1$-$C_5$alkyl; or $L_3$ and $R_2$ together form a heterocyclic ring;

$R_4$ is CN; $COR_7$; $COOR_7$; $CONR_7R_8$; $SO_2R_7$; and $R_7$ is $C_1$-$C_{22}$alkyl; or phenyl.

Preferred compounds of formula (2b) are those, wherein $R_1$ is $C_1$-$C_3$alkylene;

$L_1$, $L_2$ and $L_3$ independently form each other are hydrogen; or $C_1$-$C_5$alkyl; or $L_1$ and $L_3$ together form a carbocyclic ring;

$R_2$ is hydrogen; or $C_1$-$C_5$alkyl;

$W_1$ is $C_1$-$C_3$alkylene; or the direct bond;

$R_3$ and $R_4$ independently from each other are CN; $COR_7$; $COOR_7$; $CONR_7R_8$; $SO_2R_7$; and $R_7$ and $R_8$, independently from each other are $C_1$-$C_{22}$alkyl; or phenyl.

Furthermore, the use of compounds of formula

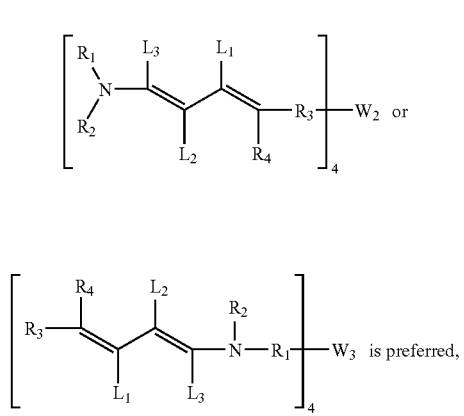

(3a)

$$\left[ \begin{array}{c} R_1 \\ R_2 \end{array} N \begin{array}{c} L_3 \\ \diagup \diagdown \\ L_2 \end{array} \begin{array}{c} L_1 \\ \diagup \diagdown \\ R_4 \end{array} R_3 \right]_4 W_2 \text{ or}$$

(3b)

$$\left[ R_3 \begin{array}{c} R_4 \\ \diagup \diagdown \\ L_1 \end{array} \begin{array}{c} L_2 \\ \diagup \diagdown \\ L_3 \end{array} \begin{array}{c} R_2 \\ N - R_1 \end{array} \right]_4 W_3 \text{ is preferred,}$$

wherein $R_1$, $R_2$, $R_3$, $R_4$, $L_1$, $L_2$, $L_3$, $W_2$ and $W_3$ are defined as in claim 1.

More preferred compounds of formula (3a) are those, wherein $L_1$, $L_2$ and $L_3$ independently from each other are hydrogen; hydroxy; $C_1$-$C_5$alkyl; or $L_1$ and $L_3$ together form a carbocyclic ring;

$R_1$ and $R_2$ independently from each other are hydrogen; or $C_1$-$C_{12}$alkyl;

$R_3$ is *—CO—$V_1$—$C_1$-$C_{12}$alkylene-**;

$V_1$ is —O—; or —NH—;

$W_2$ is a tetravalent radical of formula $$\begin{array}{c} (2) R_3 \\ \downarrow \\ *—\overset{*}{\underset{*}{C}}—* \leftarrow (3) R_3 \\ \uparrow \\ (4) R_3 \end{array}$$

$R_4$ is CN; $COR_7$; $COOR_7$; $CONR_7R_8$; $SO_2R_7$; and
$R_7$ and $R_8$, independently from each other are $C_1$-$C_{22}$alkyl; or phenyl.

Further preference is given to the use of polymeric or oligomeric compounds comprising structural elements of formula (4)

$$*\diagdown \underset{R_2}{N} \begin{array}{c} L_3 \\ \diagup \diagdown \\ L_2 \end{array} \begin{array}{c} L_1 \\ \diagup \diagdown \\ L_4 \end{array} *,$$

wherein
at least one of the asterix-marked radicals may be bound to the oligomeric or polymeric radical; and
$L_1$, $L_2$, $L_3$, $R_2$ and $R_4$ are defined as in formula (1).

Compounds of formula (4) are known and examples are disclosed in DE 3531383 on the pages 8-11.

Examples of merocyanine derivatives which are useful for the present invention are listed in the table below:

TABLE MC1a

| | $R_1$ | $R_2$ | $L_1$ | $L_2$ | $L_3$ | $R_3$ | $R_4$ |
|---|---|---|---|---|---|---|---|
| MC01 | CH$_3$ | CH$_3$ | H | H | H | —COOCH$_3$ | —COOCH$_3$ |
| MC02 | C$_2$H$_5$ | C$_2$H$_5$ | H | H | H | —COO C$_2$H$_5$ | —COOSi(CH$_3$)$_3$ |
| MC03 | C$_2$H$_5$ | C$_2$H$_5$ | H | H | H | COOC$_8$H$_{17}$-(n) | SO$_2$C$_6$H$_5$ |
| MC04 | C$_2$H$_5$ | C$_2$H$_5$ | H | H | H | CN | COOC$_8$H$_{17}$-(i) |
| MC05 | C$_4$H$_9$ | C$_4$H$_9$ | H | H | H | COOC$_6$H$_{13}$-(n) | SO$_2$C$_6$H$_5$ |
| MC06 | C$_4$H$_9$ | C$_4$H$_9$ | H | H | H | —COO C$_4$H$_9$-(n) | SO$_2$C$_6$H$_5$ |
| MC07 | C$_4$H$_9$ | C$_4$H$_9$ | H | H | H | —COO C$_4$H$_9$-(t) | *—⟨C$_6$H$_5$⟩SO$_2$— |
| MC08 | n-C$_6$H$_{13}$ | n-C$_6$H$_{13}$ | H | H | H | CN | CN |
| MC09 | i-C$_8$H$_{17}$ | i-C$_8$H$_{17}$ | H | H | H | CN | CN |
| MC10 | C$_2$H$_5$ | C$_2$H$_5$ | CH$_3$ | H | H | COOC$_2$H$_5$ | —COOSi(CH$_3$)$_3$ |
| MC11 | C$_2$H$_5$ | C$_2$H$_5$ | CH$_3$ | H | CH$_3$ | CONHC$_2$H$_5$ | —CONHC$_2$H$_5$ |
| MC12 | C$_2$H$_5$ | C$_2$H$_5$ | CH$_3$ | H | H | —CON(C$_2$H$_5$)$_2$ | —CON(C$_2$H$_5$)$_2$ |
| MC13 | C$_2$H$_5$ | C$_2$H$_5$ | CH$_3$ | H | CH$_3$ | CN | COOC$_8$H$_{17}$-(i) |
| MC14 | C$_2$H$_5$ | C$_2$H$_5$ | CH$_3$ | H | H | CN | —COOCH$_3$ |
| MC15 | C$_2$H$_5$ | C$_2$H$_5$ | CH$_3$ | H | H | SO$_2$C$_6$H$_5$ | COOC$_2$H$_5$ |
| MC16 | C$_2$H$_5$ | C$_2$H$_5$ | CH$_3$ | H | H | *—⟨C$_6$H$_5$⟩SO$_2$— | COOC$_2$H$_5$ |
| MC17 | C$_2$H$_5$ | C$_2$H$_5$ | CH$_3$ | H | CH$_3$ | —CONHC$_2$H$_5$ | —CONHC$_2$H$_5$ |
| MC18 | C$_2$H$_5$ | C$_2$H$_5$ | CH$_3$ | H | CH$_3$ | —CON(C$_2$H$_5$)$_2$ | —CON(C$_2$H$_5$)$_2$ |
| MC19 | CH$_3$ | CH$_3$ | CH$_3$ | H | CH$_3$ | CN | COOC$_8$H$_{17}$-(i) |
| MC20 | CH$_3$ | CH$_3$ | CH$_3$ | H | CH$_3$ | CN | —CON(C$_2$H$_5$)$_2$ |
| MC21 | CH$_3$ | CH$_3$ | CH$_3$ | H | CH$_3$ | *—⟨C$_6$H$_5$⟩SO$_2$— | —CONHC$_2$H$_5$ |

TABLE MC1a-continued

| | $R_1$ | $R_2$ | $L_1$ | $L_2$ | $L_3$ | $R_3$ | $R_4$ |
|---|---|---|---|---|---|---|---|
| MC22 | | | H | H | H | —SO$_2$— | COOC$_2$H$_5$ |
| MC23 | 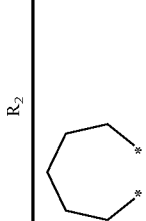 (cycloheptyl ring spanning R$_1$, R$_2$) | | CH$_3$ | H | H | | COOC$_8$H$_{17}$-(i) |
| MC24 | | | CH$_3$ | H | CH$_3$ | | COOC$_2$H$_5$ |
| MC25 | | | CH$_3$ | H | H | CN | —COO C$_2$H$_5$ |
| MC26 | 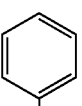 (cyclooctyl ring spanning R$_1$, R$_2$) | | CH$_3$ | H | H | —SO$_2$— | —COOSi(CH$_3$)$_3$ |
| MC27 | | | CH$_3$ | CH$_3$ | CH$_3$ | SO$_2$C$_6$H$_5$ | COOC$_8$H$_{17}$-(i) |
| MC28 | | | CH$_3$ | CH$_3$ | CH$_3$ | —SO$_2$— | SO$_2$C$_6$H$_5$ |
| MC29 | i-propyl | i-propyl | CH$_3$ | H | H | CN | |
| MC30 | CH$_3$ | CH$_3$ | CH$_3$ | H | H | CN | COOC$_8$H$_{17}$-(i) |
| MC31 | CH$_3$ | CH$_3$ | CH$_3$ | H | H | CN |  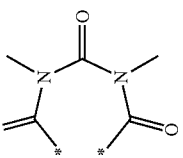 |

TABLE MC1a-continued

| | R₁ | R₂ | L₁ | L₂ | L₃ | R₃ | R₄ |
|---|---|---|---|---|---|---|---|
| MC32 | CH₃ | neopentyl-O- linker (R₂+L₃) | H | H | — | SO₂—C₆H₅ | COO-n-C₆H₁₃ |
| MC33 | CH₃ | neopentyl-O- linker (R₂+L₃) | H | H | — | CN | COO-n-C₁₂H₂₅ |
| MC34 | n-C₁₂H₂₅ | neopentyl-O- linker (R₂+L₃) | H | H | — | CN | CN |
| MC35 | n-C₁₀H₂₁ | neopentyl-O- linker (R₂+L₃) | H | H | — | *—SO₂—C₆H₅ | COOC₂H₅ |
| MC36 | CH₃ | neopentyl-O- linker (R₂+L₃) | H | H | — | *—SO₂—C₆H₅ | COO-n-C₁₀H₂₁ |

TABLE MC1a-continued
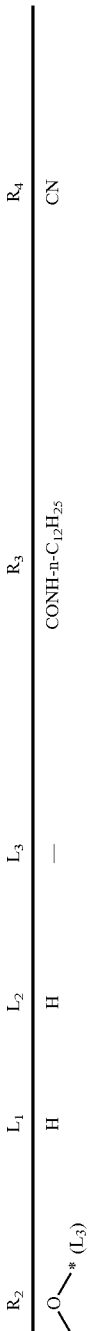
| | $R_1$ | $R_2$ | $L_1$ | $L_2$ | $L_3$ | $R_3$ | $R_4$ |
|---|---|---|---|---|---|---|---|
| MC37 | $C_2H_5$ | 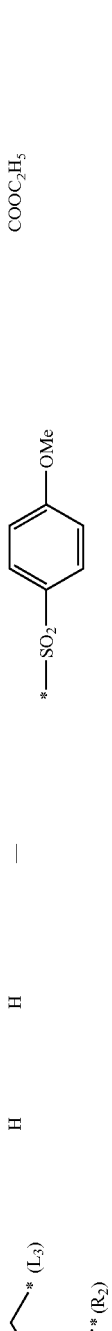 | H | H | — | $CONH\text{-}n\text{-}C_{12}H_{25}$ | CN |
| MC38 | $n\text{-}C_{10}H_{21}$ | 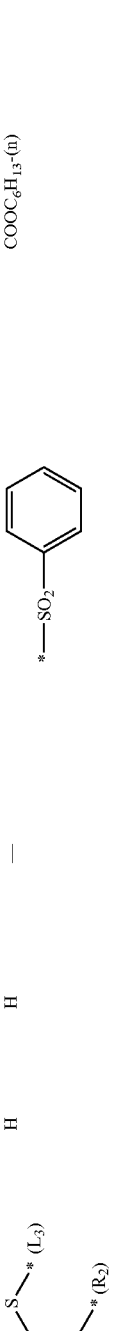 | H | H | — |  | $COOC_2H_5$ |
| MC39 | $n\text{-}C_{10}H_{21}$ |  | H | H | — |  | $COOC_6H_{13}\text{-}(n)$ |
| MC40 | $n\text{-}C_{10}H_{21}$ |  | H | H | — | $*\!-\!SO_2\text{-}n\text{-}C_6H_{13}$ | COOH |
| MC41 | $n\text{-}C_6H_{13}$ | $n\text{-}C_6H_{13}$ | H | H | H | $-COOC_2H_5$ | $*\!-\!SO_2\!-\!\text{Ph}$ |

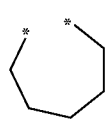

TABLE MC1a-continued

![structure: R3, R4, L1, L2, L3, N with R1, R2]

| | $R_1$ | $R_2$ | $L_1$ | $L_2$ | $L_3$ | $R_3$ | $R_4$ |
|---|---|---|---|---|---|---|---|
| MC48 | n-$C_6H_{13}$ | n-$C_6H_{13}$ | H | H | H | *—$CO_2CH_2CH_2$—O—C6H3[(t)-$C_5H_{11}$][$C_5H_{11}$-(t)] | *—$SO_2$—C6H4—CH3 |
| MC49 | n-$C_4H_9$ | n-$C_4H_9$ | H | H | H | $CO_2CH_3$ | *—$SO_2$—C6H4—C(CH3)3 |
| MC50 | \*—CH2CH2—O—CH2CH2—\* (ring) | | H | H | H | $COCH_3$ | *—$SO_2$—C6H5 |
| MC51 | n-$C_6H_{13}$ | n-$C_6H_{13}$ | H | H | H | | (N,N'-dimethyl diacyl hydrazide group) |
| MC52 | *—$(CH_2)_2$—C6H5 | n-$C_{16}H_{33}$ | H | H | H | $CO_2C_4H_9$-(n) | *—$SO_2$—C6H4—OCH3 |

TABLE MC1a-continued

| | R₁ | R₂ | L₁ | L₂ | L₃ | R₃ | R₄ |
|---|---|---|---|---|---|---|---|
| MC53 | C₂H₅ | C₂H₅ | H | H | H | COOC₁₂H₂₅-(n) | *—SO₂—C₆H₅ |
| MC54 | n-C₄H₉ | n-C₄H₉ | H | H | H | COOC₁₄H₂₉-(n) | *—SO₂—C₆H₅ |
| MC55 | H | sec-butyl | L₁ + L₃ (neopentyl bridge) | H | — | 2-ethylhexyl ester (-C(=O)O-CH₂CH(C₂H₅)C₄H₉) | CN |
| MC56 | H | n-hexyl | L₁ + L₃ (neopentyl bridge) | H | — | COOC₂H₅ | CN |
| MC57 | CH₃ | CH₃ | CH₃ | H | H | | -C(=O)-CH₂CH₂-N(CH₃)-C(=O)-* (cyclic) |

TABLE MC1a-continued

| | $R_1$ | $R_2$ | $L_1$ | $L_2$ | $L_3$ | $R_3$ | $R_4$ |
|---|---|---|---|---|---|---|---|
| MC58 | | (cyclohexyl, $R_1+R_2$) | $CH_3$ | H | H | | (dimethyl dioxy isopropylidene diester group) |
| MC59 | $CH_3$ | (cyclopentyl, $R_2+L_3$) | $CH_3$ | H | — | | (N,N'-dimethyl biuret group) |
| MC60 | H | $CH_3$ | $CH_3$ | H | $CH_3$ | | |
| MC61 | | (cycloheptyl, $R_2+R_1$) | H | $CH_3$ | H | —COOCH$_3$ | —COOCH$_3$ |
| MC62 | $CH_3$ | n-butyl | $CH_3$ | H | $CH_3$ | | (2,4-dimethyl-3-oxo-pentanedioyl group) |
| MC63 | $CH_3$ | $CH_3$ | H | H | $CH_3$ | —COOC$_2$H$_5$ | —COOC$_2$H$_5$ |

TABLE MC1a-continued

![structure: R1R2N-L3-C(L1)=C(L2)-C(R3)=C(R4)... general scaffold]

| | R₁ | R₂ | L₁ | L₂ | L₃ | R₃ | R₄ |
|---|---|---|---|---|---|---|---|
| MC64 | CH₃ | CH₃ | H | H | (tetrahydrofuran-like ring, *—*) | CN | COCH₃ |
| MC65 | CH₃ | CH₃ | CH₃ | H | H | ![N-H–C(=O)–CH₃ para-substituted phenyl, *] | ![*-C₆H₄-OCH₃ (para-methoxybenzoyl)] |
| MC66 | CH₃ | (oxepane ring with * attachments) | CH₃ | H | CH₃ | ![m-tolyl, *] | COCOOC₂H₅ |
| MC67 | CH₃ | ![neopentyl-O-*(L₃), *(R₂); R₂ + L₃] | t-butyl | H | — | CON(C₂H₅)₂ | COCH₃ |
| MC68 | i-propyl | i-propyl | (cyclopentyl ring, *,*) | (cyclopentyl ring, *,*) | H | CN | CN |
| MC69 | CH₃ | CH₃ | (cyclohexyl ring, *,*) | (cyclohexyl ring, *,*) | H | CN | CN |

TABLE MC1a-continued

| | R₁ | R₂ | L₁ | L₂ | L₃ | R₃ | R₄ |
|---|---|---|---|---|---|---|---|
| MC70 | -Si(CH₃)₂-CH₂CH₂CH₂-* | -Si(CH₃)₂-CH₂CH₂CH₂-* | CH₃ | H | H | C(=O)C(CH₃)₃ | C(=O)OC₂H₅ |
| MC71 | \*-CH₂CH₂-O-CH₂CH₂-\* (morpholine-like ring via O) | | H | CH₃ | H | -C(=O)-O-Si(CH₃)₃ | -C(=O)-O-Si(CH₃)₃ |
| MC72 | n-propyl | n-propyl | CH₃ | H | H | CO-t-butyl | -CH₂-CH(CH₃)-CH₂-O-C(=O)CH₃ with Si(OSi(CH₃)₃)₂CH₃ |
| MC73 | CH₃ | CH₃ | C₂H₅ | H | H | -C(=O)-NH-C₅H₁₁ | CN |
| MC74 | C₂H₅ | C₂H₅ | CH₃ | CH₃ | CH₃ | COOC₂H₅ | COOC₂H₅ |
| MC75 | CH₃ | CH₃ | -C(*)H-C(=O)-O-C₂H₅ | H | CH₃ | COOC₂H₅ | COOC₂H₅ |

TABLE MC1a-continued

| | $R_1$ | $R_2$ | $L_1$ | $L_2$ | $L_3$ | $R_3$ | $R_4$ |
|---|---|---|---|---|---|---|---|
| MC76 | $CH_3$ | $CH_3$ | H | *—C(=O)—O—C₂H₅ | $CH_3$ | $COOC_2H_5$ | CN |
| MC77 | $CH_3$ | $CH_3$ | *—C(=O)—O—C₂H₅ | H | *—C₆H₅ | $COOC_2H_5$ | $COOC_2H_5$ |
| MC78 | $CH_3$ | $CH_3$ | *—C₆H₄—Br | H | $CH_3$ | CN | $COOC_2H_5$ |
| MC79 | $CH_3$ | $CH_3$ | *—C₆H₄—C₆H₅ | H | $CH_3$ | CN | $COOC_2H_5$ |
| MC80 | $CH_3$ | $CH_3$ | *—CH₂—CH₂—O—* ($L_1$)($L_2$) | | H | $COOC_2H_5$ | CN |

TABLE MC1a-continued

| | R₁ | R₂ | L₁ | L₂ | L₃ | R₃ | R₄ |
|---|---|---|---|---|---|---|---|
| MC81 | CH₃ | CH₃ | *-phenyl | H | CH₃ | CN | COOC₂H₅ |
| MC82 | *-(2-methylphenyl) | CH₃ | H | H | *-CH=CH₂ (allyl) | CN | COOC₂H₅ |
| MC83 | n-butyl | n-butyl | CH₃ | H | H | COOCH₃ | *-SO₂-phenyl / *-CH₂-O-C(=O)-CH₂-Si(CH₃)₂-(attached) |
| MC84 | CH₃ | CH₃ | H | H | *-phenyl | COCH₃ | |
| MC85 | CH₃ | CH₃ | H | H | *-CH₂-O-C₂H₅ | CN | COOCH₃ |
| MC86 | CH₃ | CH₃ | *-(2-thienyl) | H | H | COOCH₃ | COOCH₃ |

TABLE MC1a-continued

![structure: R1R2N-C(L3)=C(L2)-C(L1)=C(R3)(R4)]

| | $R_1$ | $R_2$ | $L_1$ | $L_2$ | $L_3$ | $R_3$ | $R_4$ |
|---|---|---|---|---|---|---|---|
| MC87 | $CH_3$ | $CH_3$ | H | H | *–phenyl | CN | COO-t-butyl |
| MC88 | n-butyl | n-butyl | H | H | 3,4-dimethoxyphenyl* | CN | COO-t-butyl |
| MC89 | $C_2H_5$ | $C_2H_5$ | *–C6H4–F (4-F) | H | 3-CF3-phenyl* | CN | *–CH2–C(O)–O–iBu |
| MC90 | $CH_3$ | $CH_3$ | H | H | 3-CH3-phenyl* | CN | COO-i-propyl |
| MC91 | *–CH2CH(CH3)CH2CH(CH3)CH2–* | | H | H | 3-pyridyl* | CN | COO-t-butyl |

TABLE MC1a-continued

| | $R_1$ | $R_2$ | $L_1$ | $L_2$ | $L_3$ | $R_3$ | $R_4$ |
|---|---|---|---|---|---|---|---|
| MC92 | $C_2H_5$ | $C_2H_5$ | H | H | 4-methoxyphenyl-* | CN | COO—$C_2H_5$ |
| MC93 | $CH_3$ | $CH_3$ | H | H | CN | CN | COO—$CH_3$ |
| MC94 | $C_2H_5OH$ | $C_2H_5OH$ | H | H | styryl-* (PhCH=CH-*) | CN | COO—$C_2H_5$ |
| MC95 | H | $C_2H_5$ | H | H | 4-methylphenyl-* | CN | COO—$C_2H_5$ |
| MC96 | $C_2H_5$ | n-propyl | \*-(L1)-C6H4-CH2-(L2)-\* (ortho) | | H | CN | CN |

TABLE MC1a-continued
| | $R_1$ | $R_2$ | $L_1$ | $L_2$ | $L_3$ | $R_3$ | $R_4$ |
|---|---|---|---|---|---|---|---|
| MC97 | $C_2H_5$ | $C_2H_5$ | $C_2H_5$ | H | H | ![sulfonic ester chain] | ![sulfonic ester chain] |
| MC98 | $C_2H_5OH$ | $C_2H_5OH$ | $CH_3$ | $CH_3$ | H | ![carboxylic acid amide chain] | CN |
| MC99 | H | ![4-SO3Na-benzyl] | $CH_3$ | H | H | ![isobutenyl] | $COCH_3$ |

TABLE MC1a-continued

| | R₁ | R₂ | L₁ | L₂ | L₃ | R₃ | R₄ |
|---|---|---|---|---|---|---|---|
| MC100 | *−CH₂CH₂−O−CH₂CH₂−* (ring with R₂) | | C₂H₅ | H | H | *−C(=O)O−(CH₂)₄−O−CH₂CH₂−Si(C₂H₅)₃ | CN |
| MC101 | *−(CH₂)₅−* (ring with R₂) | | C₂H₅ | H | H | COOSi(CH₃)₃ | CH₂=C(−CH₂−O−C(=O)−*)−Si(CH₃)(OSi(CH₃)₃)₂ |

TABLE MC1a-continued

| | $R_1$ | $R_2$ | $L_1$ | $L_2$ | $L_3$ | $R_3$ | $R_4$ |
|---|---|---|---|---|---|---|---|
| MC102 | i-propyl | i-propyl | OH | H | H | | |
| MC103 | $CH_3$ | $CH_3$ | OH | H | H | | |
| MC104 | $CH_3$ | $CH_3$ | OH | H | H | | |
| MC105 | $CH_3$ | $CH_3$ | OH | H | H | | |

TABLE MC1a-continued
| | $R_1$ | $R_2$ | $L_1$ | $L_2$ | $L_3$ | $R_3$ | $R_4$ |
|---|---|---|---|---|---|---|---|
| MC106 | CH$_3$ |  *(L$_3$) *(R$_2$) R$_2$ + L$_3$ | OH | H | — | |  |
| MC107 | CH$_3$ | CH$_3$ | OH | H | H | | 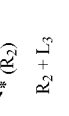 |
| MC108 | CH$_3$ | 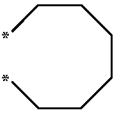 | OH | H | H | | 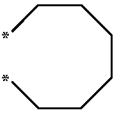 |
| MC109 | CH$_3$ | n-butyl | OH | H | H | | 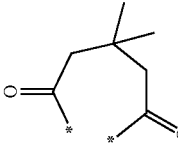 |

TABLE MC1a-continued

| | $R_1$ | $R_2$ | $L_1$ | $L_2$ | $L_3$ | $R_3$ | $R_4$ |
|---|---|---|---|---|---|---|---|
| MC110 | CH₃ | CH₃ | OH | H | ![tetrahydrofuran-2,5-diyl] | CN | COCH₃ |
| MC111 | CH₃ | CH₃ | CH₃ | H | H | 4-(NHCOCH₃)-C₆H₄- | 4-methoxybenzoyl |
| MC112 | | ![oxepane with two *] | OH | H | H | 3-methylphenyl- | ethyl 2-oxoacetate |
| MC113 | CH₃ | ![R₂+L₃ cyclic with O—*] | OH | H | — | CON(C₂H₅)₂ | COCH₃ |
| MC114 | | ![cycloheptane with two *] | OH | H | H | | phthaloyl (benzene-1,2-dicarbonyl) |

TABLE MC1a-continued

| | $R_1$ | $R_2$ | $L_1$ | $L_2$ | $L_3$ | $R_3$ | $R_4$ |
|---|---|---|---|---|---|---|---|
| MC115 | CH$_3$ | CH$_3$ | OH | H | H | | |
| MC116 | CH$_3$ | n-butyl | OH | H | H | | |
| MC117 | i-propyl | i-propyl | OH | H | H | | |
| MC118 | CH$_3$ | CH$_3$ | OH | H | H | | |

TABLE MC1a-continued

| | $R_1$ | $R_2$ | $L_1$ | $L_2$ | $L_3$ | $R_3$ | $R_4$ |
|---|---|---|---|---|---|---|---|
| MC119 | CH$_3$ | CH$_3$ | OH | H | H | | |
| MC120 | CH$_3$ | CH$_3$ | *–O–C$_6$H$_5$ | H | H | COOCH$_3$ | CN |
| MC121 | CH$_3$ | CH$_3$ | OCH$_3$ | H | H | COOCH$_3$ | CN |
| MC122 | CH$_3$ | *–cyclohexyl | OC$_2$H$_5$ | H | *–CH$_2$–C(CH$_3$)$_2$–*(R$_4$)<br>L$_3$ + R$_4$ | COOCH$_3$ | — |
| MC123 | C$_2$H$_5$ | *–C$_6$H$_4$–O–CH$_2$–*(L$_3$)<br>R$_2$ + L$_3$ | OC$_2$H$_5$ | H | — | COOC$_2$H$_5$ | COOC$_2$H$_5$ |

TABLE MC1a-continued

| | $R_1$ | $R_2$ | $L_1$ | $L_2$ | $L_3$ | $R_3$ | $R_4$ |
|---|---|---|---|---|---|---|---|
| MC124 | $CH_3$ | $CH_3$ | —O—* ($L_2$), *—($L_3$); $L_1+L_2$ | — | H | $COOC_2H_5$ | CN |
| MC125 | $CH_3$ | $CH_3$ | (structure with C=O, O—* ($L_1$), *—($R_3$)); $L_1+R_3$ | H | H | — | $COOC_2H_5$ |
| MC126 | $CH_3$ | $CH_3$ | —O—* ($L_1$), *—($L_3$); $L_1+L_3$ | H | — | $COOCH_3$ | CN |
| MC127 | $C_2H_5$ | $C_2H_5$ | H | H | H | n-$COOC_6H_{13}$ | *—$SO_2$—C$_6$H$_5$ |

MC128 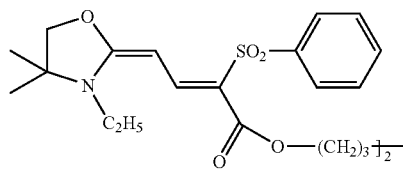
MC129 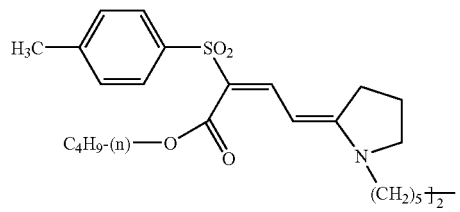
MC130 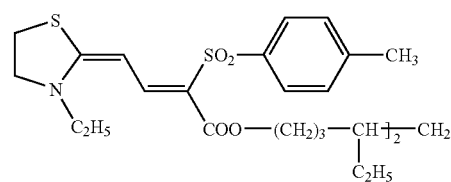
MC131 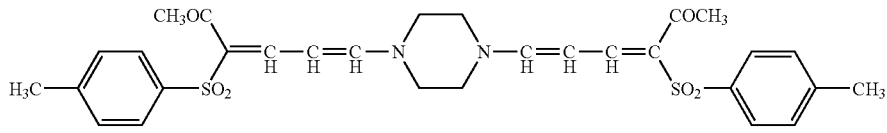
MC132 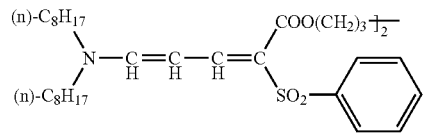
MC133 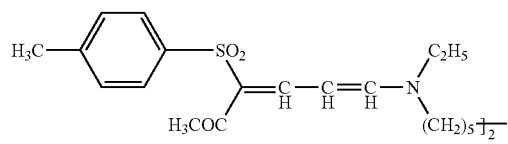
MC134 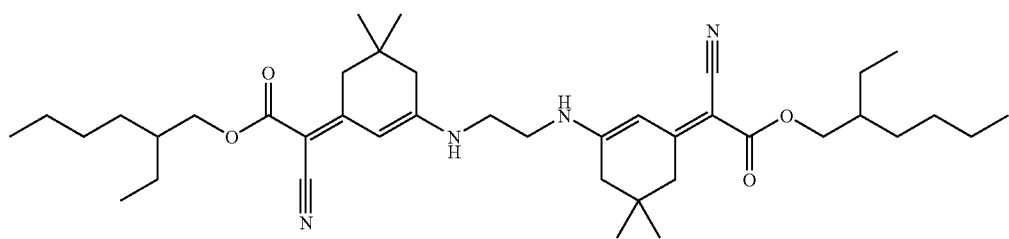 [SMILES: CCCCC(CC)COC(=O)/C(C#N)=C1/C=C(NCCNC2=C/C(=C(\C#N)C(=O)OCC(CC)CCCC)CC(C)(C)C2)CC(C)(C)C1]
MC135 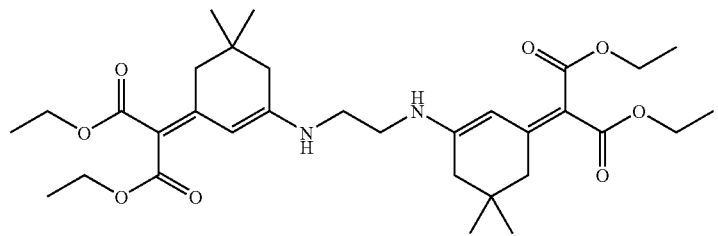 [SMILES: CCOC(=O)C(C(=O)OCC)=C1C=C(NCCNC2=CC(=C(C(=O)OCC)C(=O)OCC)CC(C)(C)C2)CC(C)(C)C1]

MC136
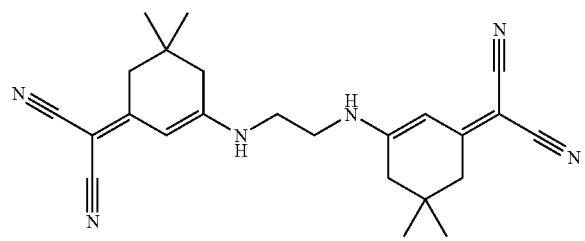 [SMILES: CC1(C)CC(NCCNC2=CC(=C(C#N)C#N)CC(C)(C)C2)=CC(=C(C#N)C#N)C1]
MC137
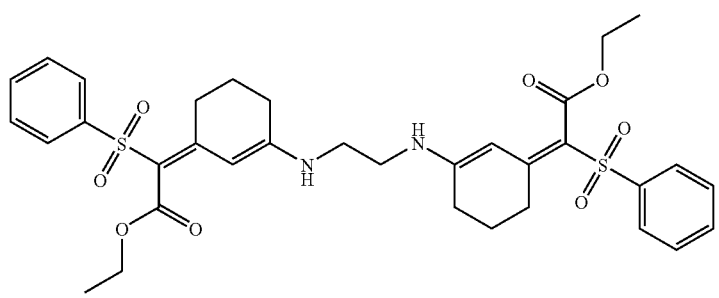 [SMILES: CCOC(=O)/C(=C1\C=C(NCCNC2=C/C(=C(\C(=O)OCC)S(=O)(=O)c3ccccc3)CCC2)CCC1)S(=O)(=O)c1ccccc1]
MC138
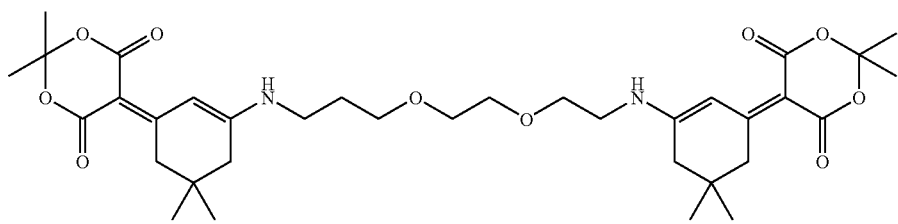
MC139
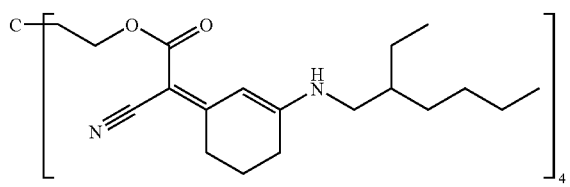
MC140
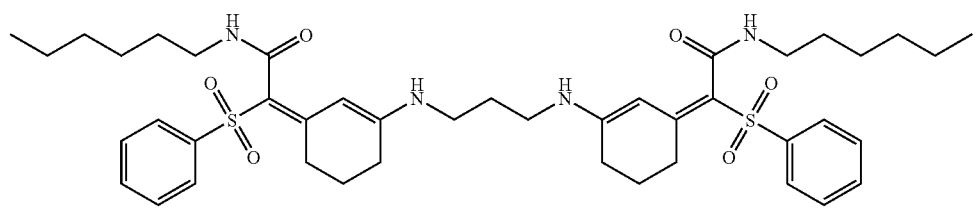 [SMILES: CCCCCCNC(=O)/C(=C1\C=C(NCCCNC2=C/C(=C(\C(=O)NCCCCCC)S(=O)(=O)c3ccccc3)CCC2)CCC1)S(=O)(=O)c1ccccc1]
MC141
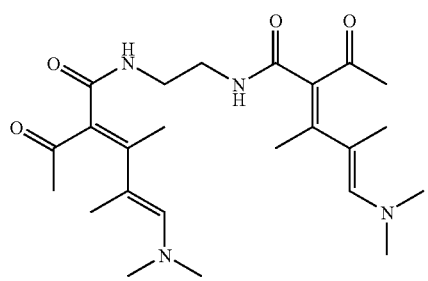 [SMILES: CC(=O)/C(C(=O)NCCNC(=O)/C(C(C)=O)=C(C)/C(C)=C/N(C)C)=C(C)\C(C)=C\N(C)C]

MC142 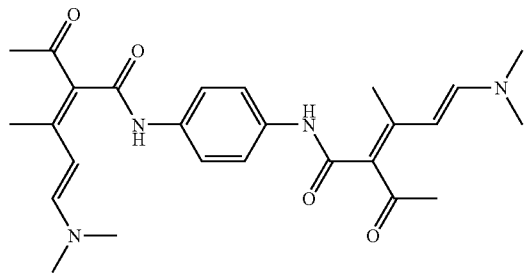 [SMILES: CC(=O)/C(C(=O)Nc1ccc(NC(=O)/C(C(C)=O)=C(C)/C=C/N(C)C)cc1)=C(C)/C=C/N(C)C]
MC143 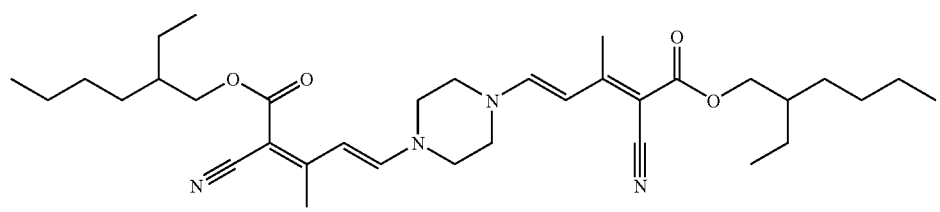 [SMILES: CCCCC(CC)COC(=O)/C(C#N)=C(C)\C=C\N1CCN(/C=C/C(C)=C(\C#N)C(=O)OCC(CC)CCCC)CC1]
MC144 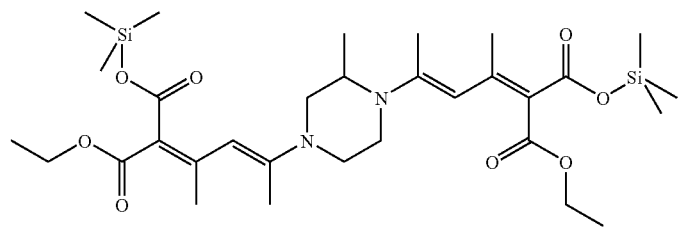 [SMILES: CCOC(=O)/C(C(=O)O[Si](C)(C)C)=C(C)/C=C(\C)N1CCN(/C(C)=C/C(C)=C(\C(=O)OCC)C(=O)O[Si](C)(C)C)C(C)C1]
MC145 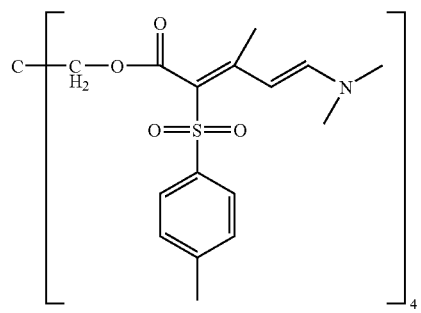
MC146 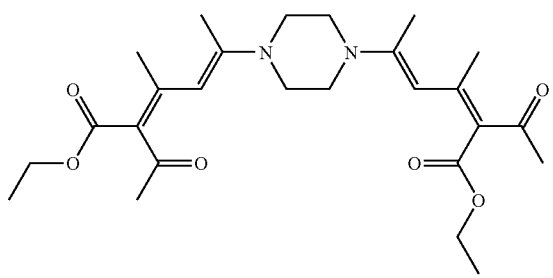 [SMILES: CCOC(=O)/C(C(C)=O)=C(C)\C=C(/C)N1CCN(/C(C)=C/C(C)=C(\C(C)=O)C(=O)OCC)CC1]
MC147 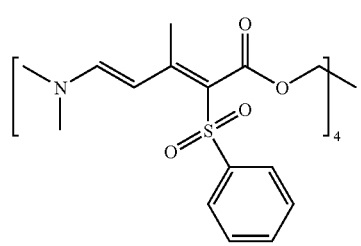

MC148 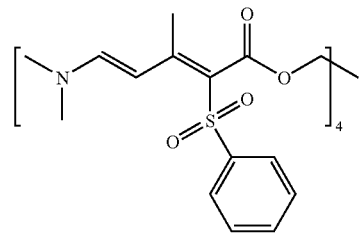
MC149 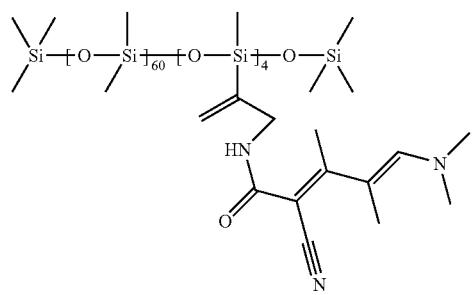
MC150 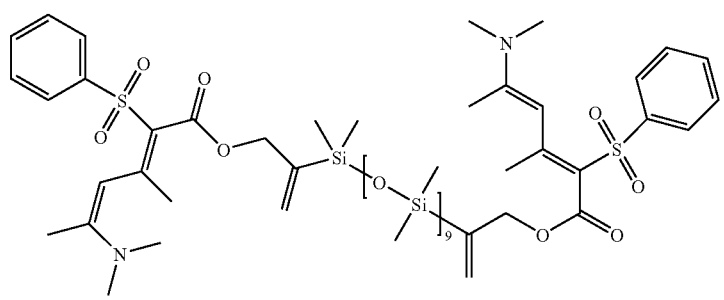
MC151 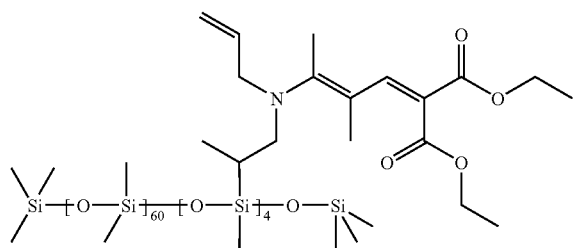
MC152 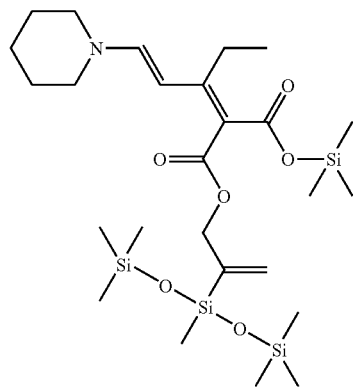 [SMILES: C=C(COC(=O)/C(C(=O)O[Si](C)(C)C)=C(\C=C\N1CCCCC1)CC)[Si](C)(O[Si](C)(C)C)O[Si](C)(C)C]

-continued
MC153
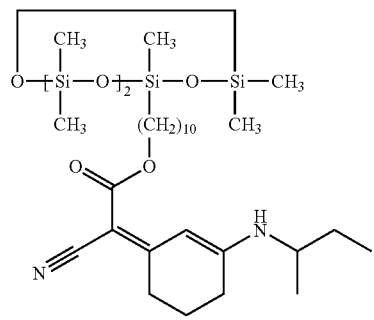
MC154
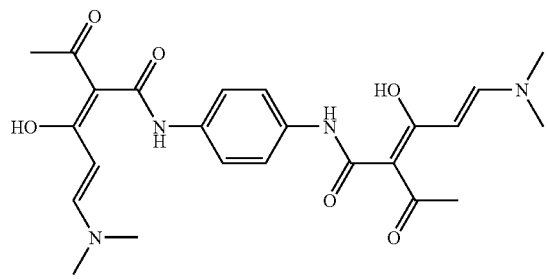 [SMILES: CC(=O)/C(C(=O)Nc1ccc(NC(=O)/C(C(C)=O)=C(O)\C=C\N(C)C)cc1)=C(O)\C=C\N(C)C]
MC155
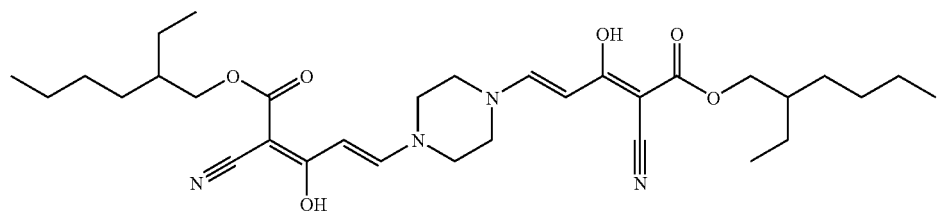 [SMILES: CCCCC(CC)COC(=O)/C(C#N)=C(O)/C=C/N1CCN(/C=C/C(O)=C(/C#N)C(=O)OCC(CC)CCCC)CC1]
MC156
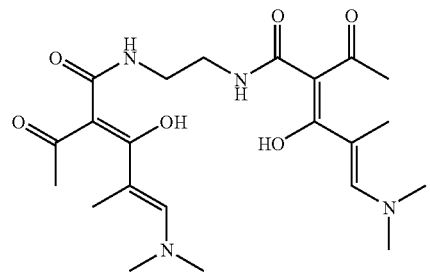 [SMILES: CC(=O)/C(C(=O)NCCNC(=O)/C(C(C)=O)=C(O)/C(C)=C/N(C)C)=C(O)\C(C)=C\N(C)C]
MC157
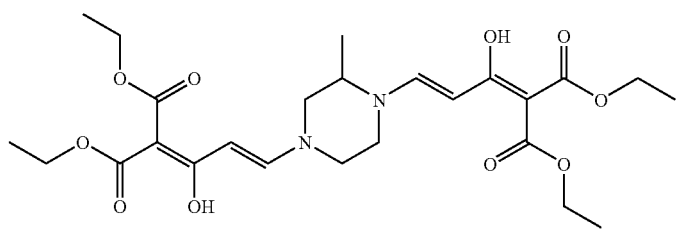 [SMILES: CCOC(=O)C(C(=O)OCC)=C(O)/C=C/N1CCN(/C=C/C(O)=C(C(=O)OCC)C(=O)OCC)C(C)C1]
MC158
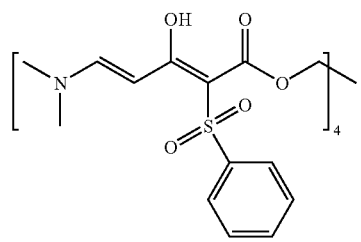

MC159
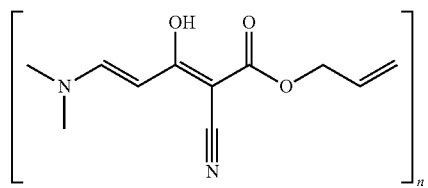
MC160
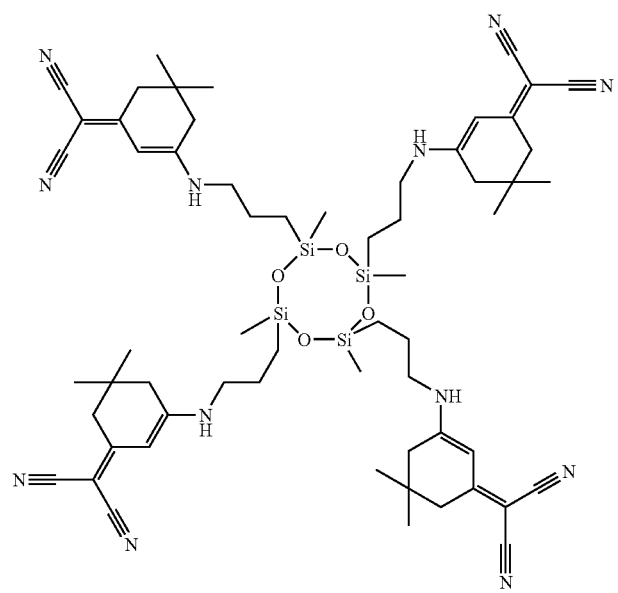
$\lambda_{max}$ = 381 nm, $\varepsilon$ = 175603 (EtOH)
MC 161
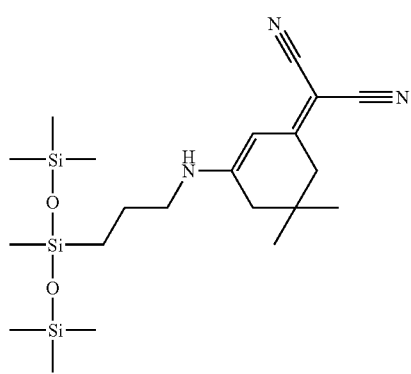
$\lambda_{max}$ = 382 nm (CH$_3$CN/H$_2$O)

MC 162
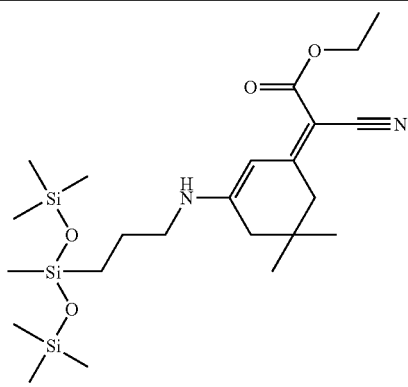
E/Z isomers
$\lambda_{max}$ = 388 nm, $\varepsilon$ = 49921 (EtOH)
MC 163
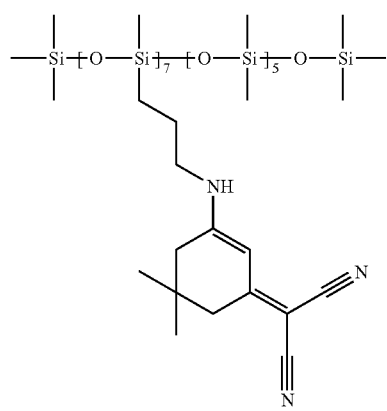
$\lambda_{max}$ = 381 nm, $\varepsilon$ = 120534 (EtOH)
MC 164
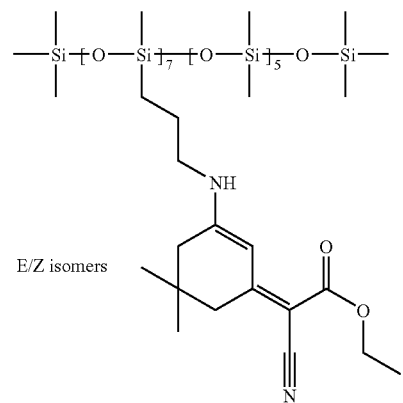
E/Z isomers
$\lambda_{max}$ = 388 nm, $\varepsilon$ = 134304 (EtOH)

MC 165
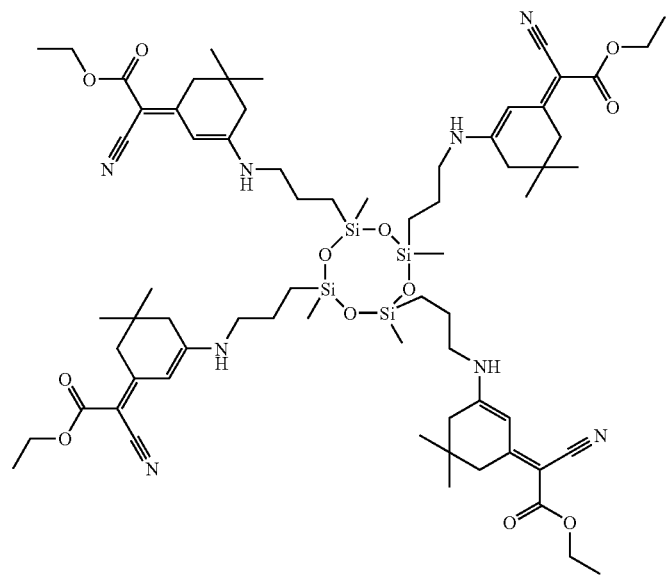
E/Z isomers
$\lambda_{max} = 388$ nm, $\varepsilon = 180128$ (EtOH)
MC 166
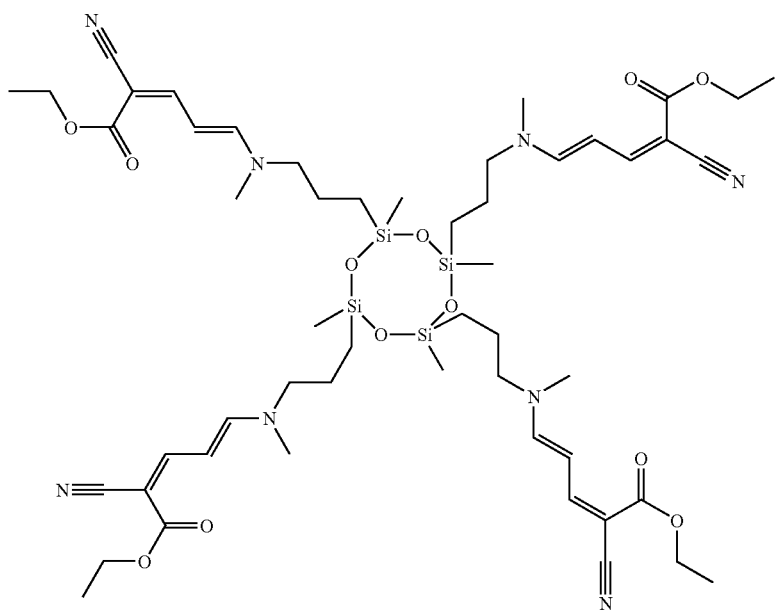
$\lambda_{max} = 381$ nm (CH$_3$CN, H$_2$O)
MC 167
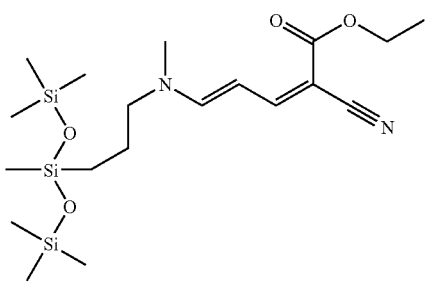
$\lambda_{max} = 381$ nm (CH$_3$CN, H$_2$O)

MC 168
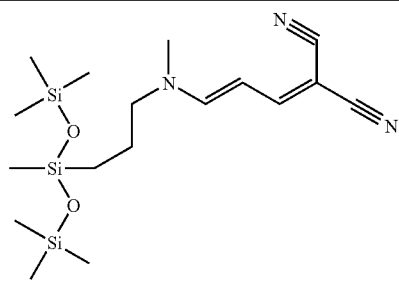
MC 169
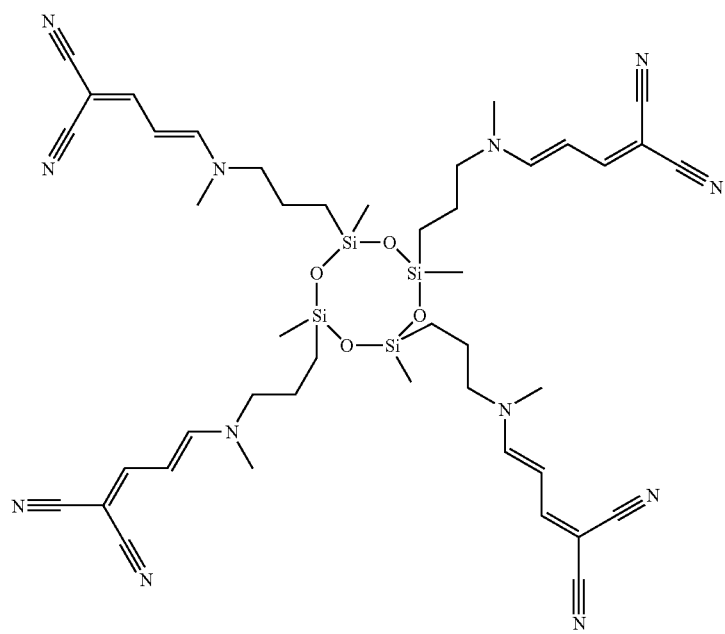 [SMILES: CN(/C=C/C=C(C#N)C#N)CCC[Si]1(C)O[Si](C)(CCCN(C)/C=C/C=C(C#N)C#N)O[Si](C)(CCCN(C)/C=C/C=C(C#N)C#N)O[Si](C)(CCCN(C)/C=C/C=C(C#N)C#N)O1]
MC 170
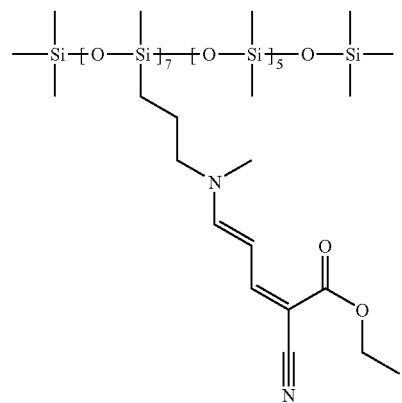
$\lambda_{max}$ = 382 nm (CH$_3$CN, H$_2$O)

MC 171

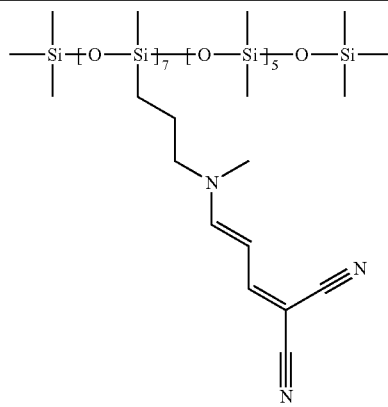

The compounds of formula (1) are known, for example from WO04/006878

Compounds however, which correspond to the formula

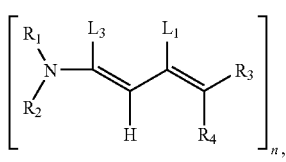

wherein $R_3$ is CN; $NR_5R_6$; —$COR_5$; —$COOR_5$; —$SO_2R_5$; —$CONR_5R_6$; $C_6$-$C_{20}$aryl; or $C_4$-$C_9$heteroaryl;

$R_4$ is CN; —$COR_7$; —$COOR_7$; —$CONR_7R_8$; $C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_5$-$C_{11}$heteroaralkyl; $C_6$-$C_{20}$aryl; $C_1$-$C_1$alkylcarbonylamino-$C_6$-$C_{20}$aryl; $C_4$-$C_9$heteroaryl;

$R_5$, $R_6$, $R_7$ and $R_8$ are independently of each other hydrogen; $C_1$-$C_{22}$alkyl, $C_2$-$C_{22}$alkenyl, $C_2$-$C_{22}$alkinyl; $C_3$-$C_{12}$cycloalkyl; $C_3$-$C_{12}$cycloalkenyl; $C_7$-$C_{20}$aralkyl; $COR_9$; —(CO)—COO—$R_9$; $C_1$-$C_{20}$heteroalkyl; $C_3$-$C_{12}$cycloheteroalkyl; $C_5$-$C_{11}$heteroaralkyl; $C_6$-$C_{20}$aryl; $C_1$-$C_5$alkoxy-$C_6$-$C_{20}$aryl; —$(CH_2)_t$—$SO_3H$; —$(CH_2)_t$—(CO)—$OR_9$; —$(CH_2)_t$—O—$C_6$-$C_{20}$aryl; —$(CH_2)_v$COO—$R_9$; $C_4$-$C_9$heteroaryl; —$(CH_2)_u$—$SiR_{15}R_{16}R_{17}$; or a radical —X-Sil;

$R_9$ is hydrogen; $C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_5$-$C_{11}$heteroaralkyl; $C_6$-$C_{20}$aryl; or $C_4$-$C_9$heteroaryl; or $L_1$ and $L_3$, are H or may be linked together to form 1, 2, 3 or 4 carbocyclic or N, O and/or S-heterocyclic rings, which may be further fused with other aromatic rings and each N in a N-heterocyclic ring may be unsubstituted or substituted by $R_{10}$;

and each alkyl, alkenyl, alkinyl, cycloalkyl or cycloalkylene group may be unsubstituted or substituted by one or more $R_{11}$;

and each aryl, heteroaryl, aralkyl, arylene, heteroarylene or aralkylene may be unsubstituted or substituted by one or more $R_{12}$;

$R_{10}$ is $R_{13}$; $COR_{13}$; $COOR_{13}$; or $CONR_{13}R_{14}$;

$R_{11}$ is halogen, OH; $NR_{15}R_{16}$; O—$R_{15}$; S—$R_{15}$; CO—$R_{15}$; oxo; thiono; CN; $COOR_{15}$; $CONR_{15}R_{16}$; $SO_2NR_{15}R_{16}$; $SO_2R_{15}$; $SO_3R_{15}$; $SiR_{15}R_{16}R_{17}$; $OSiR_{15}R_{16}R_{17}$; $POR_{15}R_{16}$; or a radical —X-Sil;

$R_{12}$ is $C_1$-$C_{12}$alkylthio; $C_3$-$C_{12}$cycloalkylthio; $C_1$-$C_{12}$alkenylthio; $C_3$-$C_{12}$cycloalkenylthio; $C_1$-$C_{12}$alkoxy; $C_3$-$C_{12}$cycloalkoxy; $C_1$-$C_{12}$alkenyloxy; or $C_3$-$C_{12}$cycloalkenyloxy which may be unsubstituted or substituted by one or more $R_{11}$; halogen; CN; SH; OH; CHO; $R_{18}$; $OR_{18}$; $SR_{18}$; $C(R_{18})$=$CR_{19}R_{20}$; O—CO—$R_{19}$; $NR_{18}R_{19}$; $CONR_{18}R_{19}$; $SO_2NR_{18}R^{19}$; $SO_2R_{18}$; $COOR_{18}$; $OCOOR_{18}$; $NR_{18}COR_{19}$; $NR_{19}COOR_{20}$; $SiR_{15}R_{16}R_{17}$; $OSiR_{15}R_{16}R_{17}$; P(=O)$R_{19}R_{20}$; or a radical —X-Sil;

$R_{13}$, $R_{14}$, $R_{15}$, $R_{16}$, $R_{17}$, $R_{18}$, $R_{19}$ and $R_{20}$ independently of each other are hydrogen; $C_1$-$C_{22}$alkyl; $C_3$-$C_{12}$cycloalkyl; $C_2$-$C_{12}$alkenyl; $C_3$-$C_{12}$cycloalkenyl; $C_6$-$C_{14}$aryl; $C_4$-$C_{12}$heteroaryl; $C_7$-$C_{18}$aralkyl; or $C_5$-$C_{16}$heteroaralkyl; or $R_{13}$ and $R_{14}$, $R_{15}$ and $R_{16}$, $R_{16}$ and $R_{17}$ and/or $R_{18}$ and $R_{19}$ may be linked together to form unsubstituted or $C_1$-$C_4$alkyl-substituted pyrrolidine, piperidine, piperazine or morpholine;

X is a linker; and

Sil is a silane-, oligosiloxane or polysiloxane moiety;

t is a number from 0 to 12;

u is a number from 1 to 12;

v is a number from 0 to 12;

if n=1

$R_1$ and $R_2$ independently of each other hydrogen; $C_1$-$C_{22}$alkyl; hydroxy-$C_1$-$C_{22}$alkyl; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_6$-$C_{20}$aryl; $C_5$-$C_1$heteroaralkyl; $C_4$-$C_9$heteroaryl; or a radical of formula

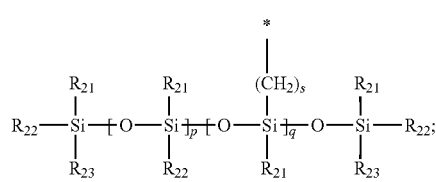

$R_{21}$, $R_{22}$, $R_{23}$ independently form each other are $C_1$-$C_{22}$alkyl; or $C_1$-$C_{22}$alkoxy;

p is a number from 0 to 100 q is a number from 1 to 20;

s is a number from 0 to 4;

$R_3$ is CN; $NR_5R_6$; —$COR_5$; —$COOR_5$; —$SO_2R_5$; —$CONR_5R_6$; $C_6$-$C_{20}$aryl; or $C_4$-$C_9$heteroaryl;

if n=2

$R_1$ and $R_2$ are each a bivalent radical selected from $C_1$-$C_5$alkylene which may be interrupted by one or more oxygen atoms; or $R_1$ and $R_2$ together with the nitrogen atoms form a six-membered heterocyclic ring; and simultaneously $R_3$ is defined as for n=1; or $R_3$ is a bivalent radical of formula —CO—$V_1$—$C_1$-$C_{12}$alkylene-$W_1$—*, wherein the asterix indicates the bond to the second $R_3$ $V_1$ is —O—; or —$NR_7$—; or the direct bond;

$W_1$ is the linkage to the second $R_3$, wherein $W_1$ is the direct bond; or selected from $C_1$-$C_{12}$alkylene; or phenylene; and $R_1$ and $R_2$ simultaneously are defined as for n=1;

if n=3 one of $R_1$, $R_2$ or $R_3$ is a trivalent radical;

if n=4

$R_1$ or $R_2$ is a radical of formula

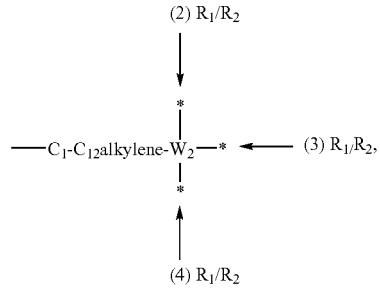

wherein the asterices indicate the bond to the second, third and fourth $R_1/R_2$;

$W_2$ is

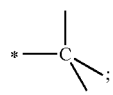

$R_3$ is defined as for n=1; or $R_3$ is a radical of formula

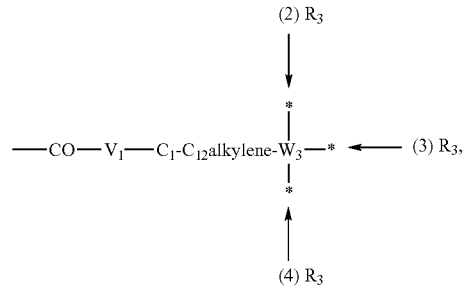

wherein the asterices indicate the bond to the second (2), third (3) and fourth (4) $R_3$; and $W_3$ is

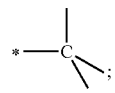

or $R_1$ or $R_2$ is a radical of formula

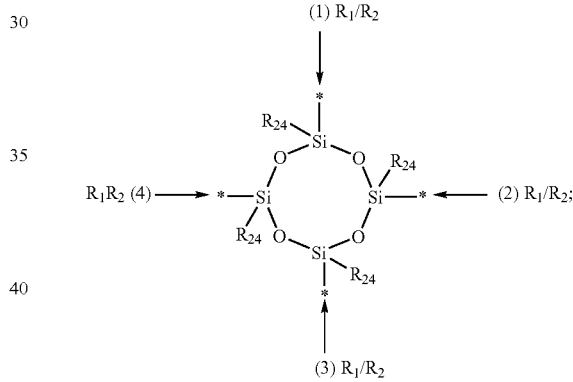

the asterices indicate the bond to the second, third and fourth $R_1/R_2$;

$R_{24}$ is $C_1$-$C_{22}$alkyl; or $C_1$-$C_{22}$alkoxy;

wherein at least one of the radicals $R_1$, $R_2$, $R_3$ or $R_4$ is a silicon organic compound, are novel and represent a further object of the present invention.

The light stabilizers of formula (1) as well as mixtures of these compounds with other UV absorbers as listed in Tables 1-3, phenolic or non-phenolic antioxidants or with complex formers are particularly suitable for protecting body-care and household products against photolytic degradation.

Examples of organic UV filters that can be used in admixture with the compounds of formula (1) are listed in the following Table:

TABLE 1

Suitable UV filter substances which can be additionally used with the compounds of formula (1)

p-aminobenzoic acid derivatives, for example 4-dimethylaminobenzoic acid 2-ethylhexyl ester;

salicylic acid derivatives, for example salicylic acid 2-ethylhexyl ester;

TABLE 1-continued

Suitable UV filter substances which can be additionally used with the compounds of formula (1)

benzophenone derivatives, for example 2-hydroxy-4-methoxybenzophenone and its 5-sulfonic acid derivative;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
polymeric UV absorbers, for example the benzylidene malonate derivatives described in EP-A-709 080;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris-(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
2-phenylbenzimidazole-5-sulfonic acid and salts thereof;
menthyl o-aminobenzoates;
physical sunscreens coated or not as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane as described in CAS 9004-73-3), dimethicone, isopropyl titanium triisostearate (as described in CAS 61417-49-0), metal soaps as magnesium stearate (as described in CAS 4086-70-8), perfluoroalcohol phosphate as C9-15 fluoroalcohol phosphate (as described in CAS 74499-44-8; JP 5-86984, JP 4-330007)).
The primary particle size is an average of 15 nm-35 nm and the particle size in dispersion is in the range of 100 nm-300 nm.
aminohydroxy-benzophenone derivatives disclosed in DE 10011317, EP 1133980 and EP 1046391
phenyl-benzimidazole derivatives as disclosed in EP 1167358
the UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

TABLE 2

Suitable UV filter substances which can be additionally used with the UV absorbers according to the present invention

| | |
|---|---|
| DE 10013318 | T 1 pp 8-9, all Examples pp 10-13, T 2 pp 13-14, all Examples p 14, Ex A, B, C, D, E, F pp 19-20 |
| DE102004038485 A1 | Formula 1 on p 2; Ex 1-4 on p 13; |
| DE102004039281 A1 | Formulas I-II on p 1; Ex Ia-Iae on pp 7-12; Ex IIa-IIm on pp 14-15; Ex 1-25 on pp 42-56; |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |

TABLE 2-continued

Suitable UV filter substances which can be additionally used with the UV absorbers according to the present invention

| | |
|---|---|
| EP 1 108 712 | 4,5-Dimorpholino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1 484051 A2 | Formula III-VII on pp18-19, Ex 7-14 on pp 7-9, Ex 18-23 on pp 11-12, Ex 24-40 on pp 14-17; |
| EP 1648849 A2 | Formula 1 on p 4; Ex 1-2 on pp 13-17; Ex C10 and O10 on pp15-16; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 848944 A2 | Formulas I and II on p 1; Ex on p 8; Examples on p 10; |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| FR 2869907 A1 | Formula 1 on p 6; T 1 on p 7-8; Ex 4-39 on pp 12-35; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 2005289916 A | Formula I on p 1; Ex Ia-Id on pp 2-3; |
| JP 2005290240 A | Formulas I on p 2, Ex II on p 2; |
| US 2003/0053966 A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911 A1 | Formula I and II on p 1; formula III and IV on p3; Ex 1-3 on pp 5-6; |
| US 2004/0071640 A1 | Ex 1-12 on pp 4-7; |
| US 2004/0091433 A1 | Ex 1-6 on pp 14-16; |
| US 2004/0136931 A1 | Ex 1-3 on p 7; |
| US 2004/0258636 A1 | Ex 1-11 on pp 9-15; |
| US 2005/0019278 A1 | Ex 1-9 on pp 6-8; |
| US 2005/0136012 A1 | Formula 1 on p 2; |
| US 2005/0136014 A1 | Formula a-c on p 2; Examples on p 3; |
| US 2005/0201957 A1 | Formula 1 on p1; Ex A, B, C, D, E, F, G on pp 2-3; |
| US 2005/0249681 A1 | all compounds on pp 2-3, Ex 1 on p 6; |
| US 2005186157 A1 | Formula 1 on p 1; Ex 1-6 on pp 2-4; |
| US 2005260144 A1 | Formula I on p1; Formula II on p 3; Ex 1-10 on pp 8-11; |
| US 2006018848 A1 | Ex a-p on pp 3-4; |
| US 2006045859 A1 | Formula 1 on p 1; Ex 1-10 on pp 2-4; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800,274 B2 | Formulas I-VI and IX-XII on pp 14-18; |

TABLE 2-continued

Suitable UV filter substances which can be additionally used with the UV absorbers according to the present invention

| | |
|---|---|
| U.S. Pat. No. 6,890,520 B2 | Ex 1-10 on pp 6-9; |
| U.S. Pat. No. 6,926,887 B2 | Ex A on pp5/6; Formulas I-VIII on pp 27-29; |
| U.S. Pat. No. 6,936,735 B2 | Formulas 1-2 on p 2; formula 3-4 on p 6; |
| U.S. Pat. No. 6,962,692 B2 | Formulas VII and VIII on p 6; Formulas I, II, IV-VI, IX, X on pp 14-16; Formula III on p 19; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 04075871 | Ex 1-3 on pp 17-18; Ex 7-9 on pp 21-22; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 05107692 A1 | Formula 1 on p 2; Ex 1-9 on pp 27-29; |
| WO 05118562 A1 | Formula I on p 4; Ex Ia-Ig on p 5; |
| WO 05121108 A1 | Formula I on p 3; Formula Ia on p 5; T 1 on p 7; Ex 3-22 on pp 11-23; |
| WO 06009451 | T 1 on pp 5-8; Formulas III and UV0 on p 9; |
| WO 06016806 | T 1 on pp 6-7; T 2 on p 10; T 3 on p 11; T 4 on p 15; |
| WO 06032741 | Formulas 1-3 on p 1; Ex a-k on pp 5-7; Ex 1-4 on pp 18-20; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

TABLE 3

Suitable UV filter substances and adjuvants which can be additionally used with the compounds of formula (1)

| No. | Chemical Name | CAS No. |
|---|---|---|
| 1 | (+/−)-1,7,7-trimethyl-3-[(4-methylphenyl)methylene]bicyclo[2.2.1]-heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; Octocrylene | 6197-30-4 |
| 30 | 2-ethylhexyl 4-(dimethylamino)benzoate | 21245-02-3 |
| 32 | 2-ethylhexyl salicylate | 118-60-5 |
| 33 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |

TABLE 3-continued

Suitable UV filter substances and adjuvants which can be additionally used with the compounds of formula (1)

| No. | Chemical Name | CAS No. |
|---|---|---|
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol]; Tinosorb M | 103597-45-1 |
| 46 | 2,4-bis{[4-(2-ethylhexyloxy)-2-hydroxy]-phenyl}-6-(4-methoxyphenyl)-(1,3,5)-triazine; Tinosorb S | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6-[[4-[[(1,1-dimethylethyl)amino]carbonyl]phenyl]-amino]1,3,5-triazine-2,4-diyl]diimino]bis-, bis(2-ethylhexyl)ester; di-ethylhexyl butamido triazone; Uvasorb HEB | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt; Tinogard HS | 92484-48-5 |
| 53 | 1-Dodecanaminium, N-[3-[[4-(dimethylamino)benzoyl]amino]propyl]-N,N-dimethyl-, salt with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate); glyceryl PABA | 136-44-7 |
| 62 | Benzeneacetic acid, 3,4-dimethoxy-α-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono no sodium salt or Disodium phenyl dibenzimidazole tetrasulfonate or Neoheliopan AP | 349580-12-7, |
| 66 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 68 | sterols (cholesterol, lanosterol, phytosterols), as described in WO0341675 | |
| 69 | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |
| 73 | silica compounds as described in EP1371356, [0033]-[0041] | |
| 74 | inorganic particles as described in DE10138496 [0043]-[0055] | |
| 75 | latex particles as described in DE10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |
| 77 | Pentanenitrile, 2-[2,3-dihydro-5-methoxy-3,3-dimethyl-6-[(2-methyl-2-propenyl)oxy]-1H-inden-1-ylidene]-4,4-dimethyl-3-oxo- | 425371-15-9 |
| 78 | Pentanenitrile, 2-(2,3-dihydro-6-hydroxy-5-methoxy-3,3-dimethyl-1H-inden-1-ylidene)-4,4-dimethyl-3-oxo- | 425371-14-8 |
| 79 | Benzenepropanenitrile, α-(2,3-dihydro-3,3,5-trimethyl-1H-inden-1-ylidene)-β-oxo- | 425371-11-5 |
| 80 | Cyclohexanepropanenitrile, α-[5-(1,1-dimethylethyl)-2,3-dihydro-3,3-dimethyl1H-inden-1-ylidene]-1-methyl-β-oxo- | 425371-10-4 |
| 81 | Pentanenitrile, 2-[6-(acetyloxy)-2,3-dihydro-5-methoxy-3,3-dimethyl-1H-inden-1-ylidene]-4,4-dimethyl-3-oxo- | 425371-09-1 |
| 82 | Pentanenitrile, 2-[2,3-dihydro-5-methoxy-3,3-dimethyl-6-[2-methyl-3-[1,3,3,3-tetramethyl-1-[(trimethylsilyl)oxy]disiloxanyl]propoxy]-1H-inden-1-ylidene]-4,4-dimethyl-3-oxo- | 425371-08-0 |
| 83 | Pentanenitrile, 2-(2,3-dihydro-5-methoxy-3,3,6-trimethyl-1H-inden-1-ylidene)-4,4-dimethyl-3-oxo- | 425371-07-9 |

TABLE 3-continued

Suitable UV filter substances and adjuvants which can be additionally used with the compounds of formula (1)

| No. | Chemical Name | CAS No. |
|---|---|---|
| 84 | Pentanenitrile, 4,4-dimethyl-3-oxo-2-(2,3,7,8-tetrahydro-8,8-dimethyl-6H-indeno[5,6-b]-1,4-dioxin-6-ylidene)- | 425371-06-8 |
| 85 | Pentanenitrile, 2-(2,3-dihydro-3,3,6-trimethyl-1H-inden-1-ylidene)-4,4-dimethyl-3-oxo- | 425371-05-7 |
| 86 | Pentanenitrile, 2-(2,3-dihydro-3,3,5,6-tetramethyl-1H-inden-1-ylidene)-4,4-dimethyl-3-oxo- | 425371-04-6 |
| 87 | Pentanenitrile, 2-(2,3-dihydro-5-methoxy-3,3,4,6-tetramethyl-1H-inden-1-ylidene)-4,4-dimethyl-3-oxo- | 425371-03-5 |
| 88 | Pentanenitrile, 2-(2,3-dihydro-5,6-dimethoxy-3,3-dimethyl-1H-inden-1-ylidene)-4,4-dimethyl-3-oxo- | 261356-13-2 |

The compounds of formula (1) may also be used in admixture with phenolic or lactone-type antioxidants as disclosed for example in WO00/25731.

The compounds of formula (1) may also be used in admixture with hindered amine light stabilizers as disclosed in WO 03/103622, e.g, hindered nitroxyl, hydroxylamine and hydroxylamine salt compounds.

Personal Care Uses

The merocyanines of formula (1) may be used as single component or in mixture with other stabilizers in particular for skin-care products, bath and shower additives, preparations containing fragrances and odoriferous substances, hair-care products, dentifrices, deodorizing and antiperspirant preparations, decorative preparations, light protection formulations and preparations containing active ingredients.

Skin-care products are, in particular, body oils, body lotions, body gels, treatment creams, skin protection ointments, shaving preparations, such as shaving foams or gels, skin powders, such as baby powder, moisturizing gels, moisturizing sprays, revitalizing body sprays, cellulite gels and peeling preparations.

Suitable bath and shower additives are shower gels, bath-salts, bubble baths and soaps.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, tooth-pastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The mentioned body-care products may be in the form of creams, ointments, pastes, foams, gels, lotions, powders, make-ups, sprays, sticks or aerosols.

They preferably contain the light stabilizers of formulae (1) and, optionally, other UV absorbers, sterically hindered amines, complexing agents and phenolic or non-phenolic antioxidants.

The present invention therefore also relates to a body-care product comprising at least one compound of formula (1).

The compounds of formula (1) are present in the body care and household products in a concentration of about 5 to about 10000 ppm, based on the total formulation, preferably from about 10 to about 5000 ppm, and most preferably from about 100 to about 1000 ppm.

The cosmetic compositions according to the present invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyidodecanol, benzoate of $C_{12}$-$C_{15}$ alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$-carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, iso-octylstearate, iso-nonylstearate, isononyl isononanoate, 2-ethylhexylpalmitate, 2-hexyllaurate, 2-hexyldecylstearate, 2-octyidodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Natural or Synthetic Triglycerides Including Glyceryl Esters and Derivatives

Di- or tri-glycerides, based on C6-C18 fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes

Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethyl isopropyl ether.

Emulsifiers

Any conventionally usable emulsifier can be used for the compositions. Emulsifier systems may comprise for example: carbocyclic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan, glucose derivatives, $C_8$-$C_{22}$ alkyl-mono and oligoglycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide amonium broide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly-(oxyethylene)$_m$-block-poly(oxypropylene)n-block (oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N dimethylammonium glycinates, cocoalkyldimethylammonium glycinate, N-acylaminopropyl-N,N-dimethylammonium glycinates, cocoacylaminopropyldimethylammonium glycinate and 2 alkyl-3-carboxymethyl-3-hydroxyethylimidazolines each having from 8 to 18 carbon atoms in the alkyl or acyl group and also cocoacylaminoethylhydroxy-ethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251.

Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20-[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N. Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Super-Fatting Agents

Substances suitable for use as super-fatting agents are, for example, lanolin andlecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers silicon dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropyl-methylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80 (steareth-10 alkyl ether/acrylates copolymer), Salcare SC81 (acrylates copolymer), Salcare SC91 and Salcare AST (sodium acrylates copolymer/PPG-1 trideceth-6), sepigel 305 (polyacrylamide/laureth-7), Simulgel NS and Simulgel EG (hydroxyethyl acrylate/sodium acryloyidimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quaternised vinylpyrrolidone/vinyl imidazole polymers, for example Luviquata (BASF), condensation products of polyglycols and amines, quaternised collagen polypeptides, for example lauryidimonium hydroxypropyl hydrolyzed collagen (LamequatâL/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinyl-pyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert. butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Cationic Surfactants cetyl trimethyl ammonium bromide (CTAB), dimethicone copolyols, amidomethicones, acrylamidopropyltrimonium chloride/Acrylamide copolymer, guar hydroxypropyl trimonium chloride, hydroxycetyl hydroxyethyl dimonium chloride quaternium compounds as listed in International Cosmetic Ingredient Dictionary and Handbook, 7th Edition 1997, for example Quaternium-80, polyquaternium compounds, as listed in International Cosmetic Ingredient Dictionary and Handbook, 7th Edition 1997, for example polyquaternium-5, polyquaternium-6, polyquaternium-7, polyquaternium-10, polyquaternium-11, polyquaternium-17, polyquaternium-18, polyquaternium-24 or polyquaternium-27, polyquaternium-28, polyquaternium-32, polyquaternium-37.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients are for example, antiperspirants, for example aluminium chlorohydrates (see J. Soc. Cosm. Chem. 24, 281 (1973)). Under the trade mark Locrona of Hoechst AG, Frankfurt (FRG), there is available commercially, for example, an aluminium chlorohydrate corresponding to formula $Al2(OH)_5Cl \times 2.5H2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)-phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Hydrotropic Agents

For improvement of the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols for that purpose comprise preferably 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives

Suitable preservatives include, for example methyl-, ethyl-, propyl-, butyl-parabens, benzalkonium chloride, 2-bromo-2-nitro-propane-1,3-diol, dehydroacetic acid, diazolidinyl urea, 2-dichloro-benzyl alcohol, dmdm hydantoin, formaldehyde solution, methyldibromoglutanitrile, phenoxyethanol, sodium hydroxymethylglycinate, imidazolidinyl urea, triclosan and further substance classes listed in the following reference: K. F. Depolo—A Short Textbook Of Cosmetology, Chapter 7, Table 7-2, 7-3, 7-4 And 7-5, P210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

Mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Other Adjuvants

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, propellants, such as propane/butane mixtures, N2O, dimethyl ether, CO2, N2 or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

The present stabilizer systems are particularly suitable for stabilizing body care products, in particular:

- skin-care preparations, e.g. skin-washing and cleansing preparations in the form of tablet-form or liquid soaps, soapless detergents or washing pastes,
- bath preparations, e.g. liquid (foam baths, milks, shower preparations) or solid bath preparations, e.g. bath cubes and bath salts;
- skin-care preparations, e.g. skin emulsions, multi-emulsions or skin oils; body oils, body lotions, body gels; skin protection ointments;
- cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;
- foot-care preparations, e.g. foot baths, foot powders, foot creams or foot balsams, special deodorants and antiperspirants or callus-removing preparations;
- light-protective preparations, such as sun milks, lotions, creams or oils, sunblocks or tropicals, pre-tanning preparations or after-sun preparations;
- skin-tanning preparations, e.g. self-tanning creams;
- depigmenting preparations, e.g. preparations for bleaching the skin or skin-lightening preparations;
- insect-repellents, e.g. insect-repellent oils, lotions, sprays or sticks;
- deodorants, such as deodorant sprays, pump-action sprays, deodorant gels, sticks or roll-ons;
- antiperspirants, e.g. antiperspirant sticks, creams or roll-ons;
- preparations for cleansing and caring for blemished skin, e.g. synthetic detergents (solid or liquid), peeling or scrub preparations or peeling masks;
- hair-removal preparations in chemical form (depilation), e.g. hair-removing powders, liquid hair-removing preparations, cream- or paste-form hair-removing preparations, hair-removing preparations in gel form or aerosol foams;
- shaving preparations, e.g. shaving soap, foaming shaving creams, non-foaming shaving creams, foams and gels, preshave preparations for dry shaving, aftershaves or aftershave lotions;
- fragrance preparations, e.g. fragrances and odoriferous substances containing preparations (scents, eau de Cologne, eau de toilette, eau de parfum, parfum de toilette, perfume), perfume oils or perfume creams;
- cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile;
- dentifrices, in particular tooth creams, toothpastes, mouthwashes, mouth rinses, anti-plaque preparations and cleaning agents for dentures;
- decorative preparations, in particular lipsticks, nail varnishes, eye shadows, mascaras, dry and moist make-up, rouge, powders, depilatory agents and suntan lotions
- cosmetic formulations containing active ingredients, in particular hormone preparations, vitamin preparations, vegetable extract preparations and antibacterial preparations.

Suitable cosmetic formulations containing active ingredients are in particular hormone preparations, vitamin preparations, vegetable extract preparations and antibacterial preparations.

Presentation Forms

The final formulations listed may exist in a wide variety of presentation forms, for example:

- in the form of liquid preparations as a W/O, O/W, O/W/O, W/O/W or PIT emulsion and all kinds of microemulsions,
- in the form of a gel,
- in the form of an oil, a cream, milk or lotion,
- in the form of a stick, in the form of a spray (spray with propellent gas or pump-action spray) or an aerosol,
in the form of a foam, or
in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition:
0.01 to 5% by weight of the compound of formula (1),
12.0% by weight of sodium laureth-2-sulfate,
4.0% by weight of cocamidopropyl betaine,
3.0% by weight of sodium chloride,
and water ad 100%.

For example, especially the following hair-cosmetic formulations may be used:
a1) spontaneously emulsifying stock formulation, comprising the compound of formula (1) according to the invention, optionally another stabilizer, PEG-6-C10oxoalcohol and sorbitan sesquioleate, to which water and any desired quaternary ammonium compound, for example 4% minkamidopropyl dimethyl-2-hydroxyethylammonium chloride or Quaternium 80 is added;
a2) spontaneously emulsifying stock formulation comprising the compound of formula (1) according to the invention, optionally another stabilizer, tributyl citrate and PEG-20-sorbitan monooleate, to which water and any desired quaternary ammonium compound, for example 4% minkamidopropyl dimethyl-2-hydroxyethylammonium chloride or Quaternium 80 is added;
b) quat-doped solutions comprising the compound of formula (1) according to the invention in butyl triglycol and tributyl citrate; and optionally another stabilizer;
c) mixtures or solutions comprising the compound of formula (1) according to the invention with alkylpyrrolidone; and optionally another stabilizer.

Examples of body care products of the present invention are listed in the Table below:

| Body care product | Ingredients |
| --- | --- |
| moisturising cream | vegetable oil, emulsifier, thickener, perfume, water, antioxidant, UV absorbers |
| shampoo | surfactant, emulsifier, preservatives, perfume, antioxidant, UV absorbers |
| Toothpaste | cleaning agent, thickener, sweetener, flavor, colorant, antioxidant, water, UV absorbers |
| lip-care stick | vegetable oil, wax, $TiO_2$, antioxidant, UV absorbers |

Household Products

The stabilizer systems of the present invention are also used in household cleaning and treatment agents, for example in laundry products and fabric softeners, liquid cleansing and scouring agents, glass detergents, neutral cleaners (all-purpose cleaners), acid household cleaners (bath), bathroom cleaners, WC cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multipurpose polishes and leather and vinyl dressing agents (leather and vinyl sprays) and air fresheners.

Household cleaning agents are aqueous or alcoholic (ethanol or isopropyl alcohol) solutions of one or more of the following components:
anionic, nonionic, amphoteric and/or cationic surfactants
soaps, prepared by saponification of animal and vegetable greases
organic acids, like hydrochloric acid, phosphoric acid, or sulfuric acid,
for basic products inorganic (NaOH or KOH) or organic bases;
abrasives for improved cleaning of surfaces,
waxes and/or silicones for maintenance and protection of surfaces,
polyphosphates,
substances which eliminate hypochlorite or halogens;
peroxides comprising bleaching activators like TAED, for example sodium perborate or $H_2O_2$;
enzymes;
in washing detergents discoloration inhibitors, soil-release compounds, grey scale inhibitors, foam inhibitors, fluorescent whitening agents;
cleaning agents based on wax may comprise solvents selected from benzine, turpentine and/or paraffines and emulsifiers based on wax;
filling agents like silicates, polyphosphates, Zeolithes for powdery cleaning agents;
pigments, lakes or soluble dyes;
perfumes; and
light stabilizers, antioxidants and chelating agents.

Colored cleaning agents and decorative cosmetic products can comprise the following dyes:
inorganic pigments, for example iron oxide (Iron Oxide Red, Iron Oxide Yellow, Iron Oxide Black, etc.), Ultramarines, Chromium Oxide Green or Carbon Black;
natural or synthetic orgnic pigments;
disperse dyes which may be solubilzed in solvents like direct hair dyes of the HC type, for example HC Red No. 3, HC Blue No. 2 and all other hair dyes listed in International Cosmetic Ingredient Dictionary and Handbook, 7th edition 19997) or the dispersion dyes listed in Color Index International or Society of Dyers and Colourists;
color varnishes (insoluble salts of soluble dyes, like many Ca-, Ba- or Al-salts of anionic dyes);
soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wave length of ca. 4000 to 700 nm). The absorption is often caused by the following chromophores:
Azo- (mono-, di, tris-, or poly-)stilbene-, carotenoide-, diarylmethan-, triarylmethan-, xanthen-, acridin-, quinoline, methin- (also polymethin-), thiazol-, indamin-, indophenol-, azin-, oxazin, thiazin-, anthraquinone-, indigoid-, phtalocyanine- and further synthetic, natural and/or inorganic chromophores.

The present invention also relates to home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets. The present invention also relates to home care products such as candles, gel candles, air fresheners and fragrance oils (for the home).

Typical examples of household cleaning and treating agents are listed in the table below:

| Household cleaners/ household treating agents | Ingredients |
| --- | --- |
| detergent concentrate | surfactant mixture, ethanol, antioxidant, water, UV absorbers, antioxidants |
| shoe polishwax | wax emulsifier, antioxidant, water, preservative, UV absorbers, antioxidants |
| wax-containing floor cleaning agent | emulsifier, wax, sodium chloride, light stabiliser of formulae (1) and (2), water, preservative UV absorbers, antioxidant |

The stabilizers of formula (1) according to the present invention are for example incorporated by dissolution in an oil phase or alcoholic or water phase, where required at elevated temperature.

The present body care products and household products have high stability towards color changes and chemical degradation of the ingredients present in these products. For example, present compositions that comprise a dye are found to have excellent color stability.

The following Examples illustrate the invention.

In the following Examples the stabilizers listed in the Table below have been used:

Comp. of formula   Structure (101)
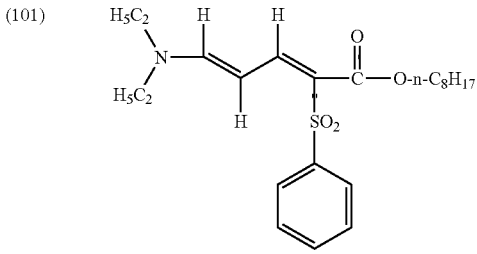

(102)
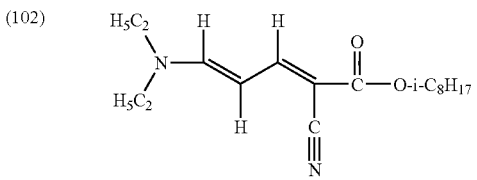

(103)
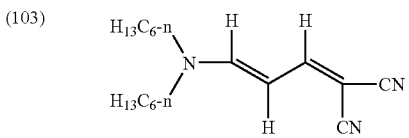

(104)
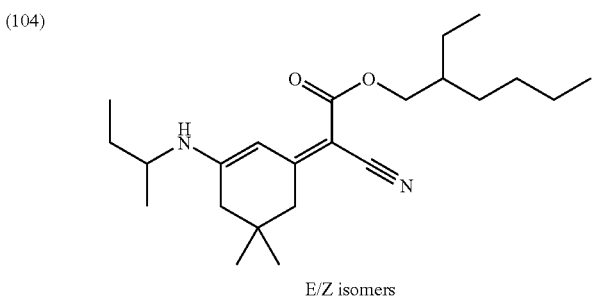

E/Z isomers

| Comp. of formula | Structure |
|---|---|
| (105) | 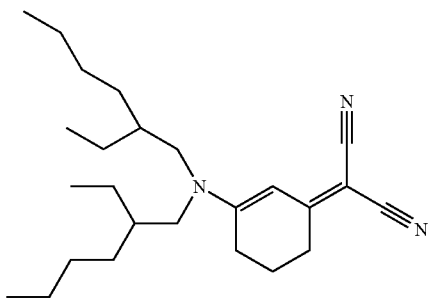 [SMILES: CCCCC(CC)CN(CC(CC)CCCC)C1=CC(=C(C#N)C#N)CCC1] |
| AO 01 | 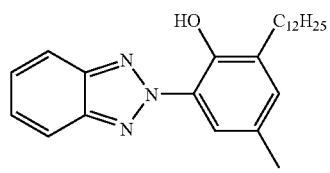 |
| AO 02 | 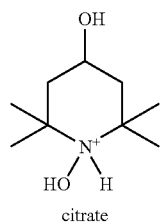 citrate |
| AO 03 | 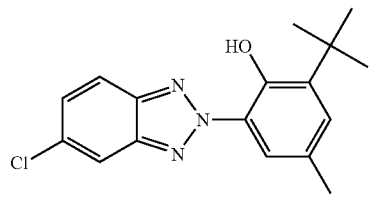 [SMILES: Cc1cc(-n2nc3ccc(Cl)cc3n2)c(O)c(C(C)(C)C)c1] |
| AO 04 | 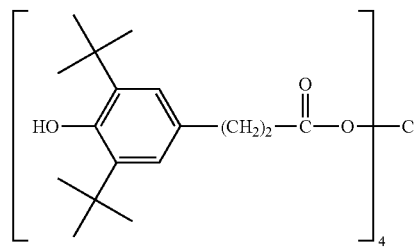 |
| AO 05 | 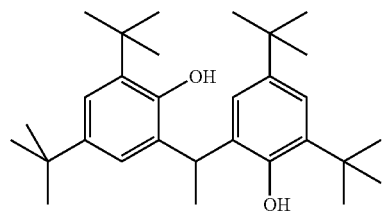 [SMILES: CC(c1cc(C(C)(C)C)cc(C(C)(C)C)c1O)c1cc(C(C)(C)C)cc(C(C)(C)C)c1O] |

| Comp. of formula | Structure |
|---|---|
| AO 06 | 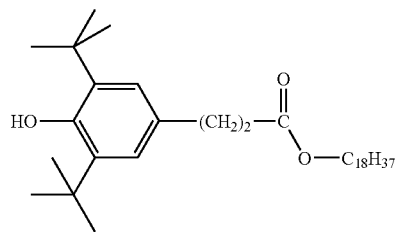 |
| AO 07 | 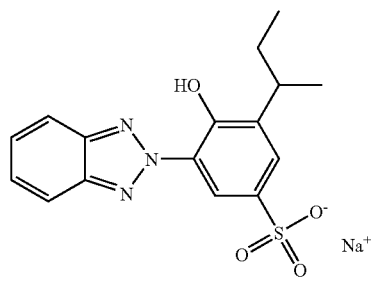 [SMILES: CCC(C)c1cc(S(=O)(=O)[O-])cc(-n2nc3ccccc3n2)c1O ; [Na+]] |

Efficacy Comparison to State-of-the Art Stabilizers

EXAMPLE 1

The following colored basic shampoo formulation is prepared:

| Sodium Laureth Ether Sulfate | 10% |
|---|---|
| Cocamidopropylbetaine | 3% |
| Citric Acid | to pH 5 |
| FD & C Blue No. 1 | 0.002% |
| Stabilizer | q.a. |

The following stabilized und unstabilized samples of this formulation are prepared for light stability testing:
1. unstabilized basic shampoo formulation
2. basic shampoo formulation plus 0.05% of the compound of formula (AO 07)
3. basic shampoo formulation plus 0.05% of compound of formula (101)
4. basic shampoo formulation plus 0.05% of compound of formula (102)
5. basic shampoo formulation plus 0.05% of compound of formula (103)
6. basic shampoo formulation plus 0.05% of compound of formula (104)
7. basic shampoo formulation plus 0.05% of compound of formula (105)

The formulations were filled into 30 ml glass bottles and irradiated in an ATLAS Suntest XLS+Xenon Lamp (light intensity 500 W/m2, spectrum of light adjusted to indoor conditions, sample chamber temperature: 32° C.).

The results are listed in the table below.

| Sample | Irradiation Time until samples were significantly faded |
|---|---|
| 1 | 8 hours (colorless) |
| 2 | 15 hours (colorless) |
| 3 | 21 hours (faded, but still colored) |
| 4 | 70 hours (faded, but still colored) |
| 5 | 70 hours (faded, but still colored) |
| 6 | 70 hours (faded, but still colored) |
| 7 | 40 hours (faded, but still colored) |

Sample 3-7 comprising a stabilizer according to the present invention exhibits significantly better light stability compared to the state-of-the-art UV absorber of formula (AO 07).

EXAMPLE 2

The following colored basic shampoo formulation is prepared:

| Sodium Laureth Ether Sulfate | 10% |
|---|---|
| Cocamidopropylbetaine | 3% |
| Citric Acid | to pH 5 |
| FD&C Blue No. 1 | 0.002% |
| Stabilizer | q.a. |

The following stabilized und unstabilized samples of this formulation are prepared for light stability testing:
1. unstabilized basic shampoo formulation
2. basic shampoo formulation plus 0.05% of the compound of formula (AO 07)
3. basic shampoo formulation plus 0.05% of the compound (AO 07) plus 0.003% or compound AO 02
4. basic shampoo formulation plus 0.05% of compound of formula (104).

The formulations were filled into 30 ml glass bottles and irradiated in an ATLAS Suntest XLS+ Xenon Lamp (light intensity 500 W/m2, spectrum of light adjusted to indoor conditions, sample chamber temperature: 32° C.).

The results are listed in the table below.

| Sample | Irradiation Time until samples were significantly faded |
|---|---|
| 1 | 8 hours |
| 2 | 25 hours |
| 3 | 45 hours |
| 4 | 65 hours |

Sample 4 comprises a stabilizer according to the present invention. It exhibits significantly better light stability compared to the state-of-the-art UV absorber of formula (AO 01), and performed even better than the highly effective stabilizer combination of sample 3.

EXAMPLE 3

The following stabilized and unstabilized samples were prepared for antioxidation testing:
1. pure linoleic acid
2. linoleic acid containing 0.05% of compound of formula (104).

The samples were placed in a RACIMAT and heated to 80° C. An airflow of 15 L/min was adjusted. The airstream bubbles through each heated sample and afterwards through a water reservoir. Thus all volatile organic compounds formed by the oxidation process are carried into the water reservoir by the airstream. The conductivity of the water reservoir is monitored online during the measurement. Once oxidation starts volatile organic compounds like formic acid are transported into the water reservoir which results in a rapid (exponential) increase of conductivity. The time until oxidation starts is called "induction time".

The results are listed in the table below.

| Sample | Induction Time |
|---|---|
| 1 | 1.15 hours |
| 2 | 1.98 hours |

Sample 2 comprising a stabilizer according to the present invention exhibits better oxidation stability compared to the unstabilized sample.

EXAMPLE 4-15

Preparation of Body-Care and Household Formulations

| Example 4: Preparation of a sprayable hair styling gel | | | |
|---|---|---|---|
| Phase | Ingredients | (w/w) % | |
| A | carbomer (1% dispersion) | 0.30 | |
|   | water, demin. | 30.00 | |
| B | glycerol | 2.00 | |
|   | methylparaben | 0.20 | |
| C | water, demin. | ad 100 | |
|   | PVP/VA copolymer | 8.00 | |
|   | triethanolamine (88%) | 0.12 | |
|   | EDTA, disodium salt | 0.01 | |
|   | light stabilizer of formula (101) | 0.10 | |

Preparation:

The components (A) are dispersed at room temperature.

(B) is mixed under heating until the paraben is completely dissolved and then (B) is added with gentle stirring to (A).

(C) is blended until it is completely dissolved and is slowly added under stirring to the mixture of (A) and (B).

The transparency of the gel can be increased by adding small amounts of triethanolamine (pH=5.6-5.75).

| Example 5: Preparation of a baby shampoo | |
|---|---|
| Ingredients | (w/w) % |
| cocoamidopropylbetaine | 35.00 |
| water, demin. | ad.100 |
| citric acid | q.s. (pH) |
| polyquaternium-15 | 0.15 |
| perfume oil | 0.30 |
| chlorophyll | 0.20 |
| light stabilizer of formula (102) | 0.02 |
| Compound of formula (AO 01) | 0.02 |
| colorant (D&C Yellow No. 5) | 0.02 |
| sodium chloride | 0.30 |

Preparation:

Surfactant and water are blended until a homogeneous solution is obtained. The pH is adjusted to 6.0-6.5 with citric acid and the other components are added in the indicated sequence. The mixture is stirred until it is completely dissolved.

| Example 6: Preparation of a perfumed toilet water | |
|---|---|
| Ingredients | (w/w) % |
| ethanol, 96% | 60 |
| d-limonene | 5 |
| cedrene | 1.5 |
| citronellol | 0.5 |
| savin | 0.5 |
| light stabilizer of formula (103) | 0.05 |
| light stabilizer of formala (AO 01) | 0.05 |
| light stabilizer of formula (AO 02) | 0.03 |
| Antioxidant of formula (AO 06) | 0.02 |
| S,S-EDDS | 0.01 |
| colorant (D&C Yellow No. 5) | 0.1 |
| water | ad. 100 |

Preparation:

The components are thoroughly mixed in the indicated sequence at 50° C. A clear homogeneous solution is obtained.

| Example 7: Preparation of a lipstick, non-greasy | |
|---|---|
| Ingredients | (w/w) % |
| Carnauba wax | 2.5 |
| Beeswax, white | 20.0 |
| Ozekerite | 10.0 |
| Lanoline, anhydrous | 5.0 |
| Cetyl alcohol | 2.0 |
| Liquid paraffin | 3.0 |
| Isopropyl Myristate | 3.0 |
| Propylene glycol recinoleate | 4.0 |
| CI Pigment Red 4 | 9.0 |
| CI Pigment Blue 15 | 1.0 |
| Light stabilizer of formula (101) | 0.1 |
| Castor Oil | ad 100 |

Example 8: Preparation of a lipstick, transfer resistant

| Ingredients | (w/w) % |
|---|---|
| Cyclomethicone | 41.50 |
| Isodecane | 10.00 |
| D&C Red No. 7 | 8.00 |
| Synthetic wax | 6.00 |
| Isostearyltrimethylpropane siloxysilicate | 5.00 |
| Cetylstearate/acetylated lanolin, 90:10 | 5.00 |
| Ceresin | 4.00 |
| Paraffin | 3.00 |
| Titanium dioxide | 2.00 |
| Methylparaben | 0.30 |
| Propylparaben | 0.10 |
| Antioxidant of formula (AO 04) | 0.10 |
| light stabilizer of formula (101) | 0.10 |

Example 9: Preparation of a Rouge (powder)

| Ingredients | (w/w) % |
|---|---|
| Talcum | 56 |
| Zinc Stearate | 15 |
| Rice starch | 15 |
| Iron Oxide Red | 12 |
| Perfume | q.s. |
| light stabilizer of formula (101) | 0.1 |

Example 10: Preparation of a Foundation cream

| Ingredients | (w/w) % |
|---|---|
| Titanium dioxide | 12.79 |
| Oleyl alcohol | 4.57 |
| Glyceryl stearate | 3.65 |
| Propylene glycol | 3.65 |
| Stearic acid | 1.83 |
| Magnesium aluminium silicate | 0.91 |
| Triethanolamine 99% | 0.91 |
| Iron Oxide Yellow | 0.64 |
| Iron Oxide Red | 0.32 |
| CI Pigment Brown 6 | 0.37 |
| Carboxymethyl cellulose | 0.10 |
| light stabilizer of formula (101) | 0.10 |
| Water | ad 100 |

Example 11: Preparation of an Eyeliner

| Ingredients | (w/w) % |
|---|---|
| Polysaccharide resin (Kama KM 13, Kama) | 8.00 |
| Iron Oxide Black | 6.50 |
| Carnauba wax | 1.00 |
| Triethanolamin, 99% | 1.00 |
| Hydrogenated polyisobutane | 1.00 |
| Hydrogenated polydecene | 1.00 |
| Sorbitan sesquioleate | 1.00 |
| Xanthum gum | 0.50 |
| Polysaccharide resin (Kama KM 13, Kama) | 8.00 |
| Carboxymethyl cellulose | 0.40 |
| Magnesium aluminium silicate | 0.40 |
| Methyl paraben | 0.35 |
| Stearic acid | 2.50 |
| Lecithin | 0.20 |
| Imidazolidinyl urea | 0.10 |
| light stabilizer of formula (102) | 0.10 |
| Antioxidant of formula (AO 05) | 0.05 |
| Water | to 100 |

Example 12: Preparation of an Eyelash Makeup

| Ingredients | (w/w) % |
|---|---|
| Paraffin Wax | 10.00 |
| Starch | 5.00 |
| Polyethylene | 5.00 |
| Iron Oxide Black | 7.00 |
| Carbomer (Carbopol, BFGoodrich) | 0.50 |
| Hydroxyethylcellulose | 0.50 |
| Panthenol | 2.00 |
| Light stabilizer of formula (103) | 0.05 |
| Water | ad 100 |

Example 13: Preparation of a Nail Varnish

| Ingredients | (w/w) % |
|---|---|
| Poly(1-trimethylsilylpropylene) | 0.30 |
| Nitrocellulose | 12.00 |
| Alkyd resin | 10.00 |
| Dibutyl phthalate | 4.00 |
| Camphor | 2.00 |
| Butyl acetate | 49.50 |
| Toluene | 20.00 |
| Pigment Red 57.1 | 1.00 |
| Quaternary bentonite | 1.00 |
| Light stabilizer of formula (101) | 0.20 |
| Light stabilizer of formula (AO 03) | 0.10 |

Preparation of Formulations of Household Products

Example 14: Preparation of a green-colored glass detergent:

| Ingredients | (w/w) % |
|---|---|
| anionic/amphoteric surfactants (Lumorol RK) | 0.7 |
| butyl glycol | 5.0 |
| isopropanol | 20.0 |
| d-limonene | 4.00 |
| colorant (D&C Green No. 2) | 0.05 |
| light stabilizer of formula (AO 02) | 0.05 |
| light stabilizer of formula (102) | 0.05 |
| water, demin. | ad. 100 |

Preparation:
The components are dissolved in the indicated sequence until a clear homogeneous mixture is obtained.

Example 15: Preparation of a floor wax

| Ingredients | (w/w) % |
|---|---|
| wax mixture | 12 |
| white spirit | ad 100 |
| d-limonene | 4.00 |
| light stabiliser of formula (103) | 0.10 |

Preparation:
The components are stirred in the indicated sequence until a homogeneous mixture is obtained.

The invention claimed is:
1. A method for protecting body-care and household products from photolytic and oxidative degradation wherein said body-care and household products are stored in a container, said container has a low absorption in the UV-A range said method comprises adding to said body-care and household products about 5 to about 10000 ppm of at least one stabilizer of formula

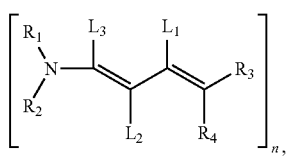

(1)

wherein
- $L_1$, $L_2$ or $L_3$ independently of each other hydrogen; hydroxy; $C_1$-$C_{22}$alkyl; $C_1$-$C_{22}$alkoxy; $C_2$-$C_{22}$alkenyl; $C_2$-$C_{22}$alkynyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cyclo-heteroalkyl, $C_5$-$C_{11}$heteroaralkyl; $C_6$-$C_{20}$aryl; $C_6$-$C_{20}$aryl-$C_1$-$C_5$alkenylene; $C_4$-$C_9$heteroaryl; CN; —$(CH_2)_t$—$OR_9$; or $COOR_9$;
- $R_4$ is CN; —$COR_7$; —$COOR_7$; —$SO_2R_7$; —$CONR_7R_8$; $C_1$-$C_{22}$alkyl; $C_2$-$C_{22}$alkenyl; $C_2$-$C_{22}$alkynyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_5$-$C_{11}$heteroaralkyl; $C_6$-$C_{20}$ aryl; $C_1$-$C_4$alkylcarbonylamino-$C_6$-$C_{20}$aryl; $C_4$-$C_9$heteroaryl;
- $R_5$, $R_6$, $R_7$ and $R_8$ are independently of each other hydrogen; $C_1$-$C_{22}$alkyl, $C_2$-$C_{22}$alkenyl, $C_2$-$C_{22}$alkynyl; $C_3$-$C_{12}$cycloalkyl; $C_3$-$C_{12}$cycloalkenyl; $C_7$-$C_{20}$ aralkyl; $COR_9$; —(CO)—COO—$R_9$; $C_1$-$C_{20}$ heteroalkyl; $C_3$-$C_{12}$cycloheteroalkyl; $C_5$-$C_{11}$heteroaralkyl; $C_6$-$C_{20}$ aryl; $C_1$-$C_5$alkoxy-$C_6$-$C_{20}$aryl; —$(CH_2)_t$—$SO_3H$; —$(CH_2)_t$—(CO)—$OR_9$; —$(CH_2)_t$—O—$C_6$-$C_{10}$aryl; —$(CH_2)_v$COO—$R_9$; $C_4$-$C_9$heteroaryl; —$(CH_2)_u$—$SiR_{15}R_{16}R_{17}$; or a radical —X-Sil;
- $R_9$ is hydrogen; $C_1$-$C_{22}$alkyl; $C_2$-$C_{22}$alkenyl; $C_2$-$C_{22}$alkynyl; $C_3$-$C_{12}$cycloalkyl; $C_3$-$C_{12}$cycloalkenyl; $C_7$-$C_{20}$ aralkyl; $C_1$-$C_{20}$heteroalkyl; $C_3$-$C_{12}$cycloheteroalkyl; $C_5$-$C_{11}$heteroaralkyl; $C_6$-$C_{20}$aryl; or $C_4$-$C_9$heteroaryl; or
- $L_1$ and $L_2$, $L_1$ and $L_3$, $L_2$ and $L_3$, $L_1$ and $R_4$, $L_2$ and $R_4$, $L_1$ and $R_1$, $L_2$ and $R_1$, $L_3$ and $R_1$, $L_3$ and $R_5$, $R_3$ and $R_4$, $R_1$ and $R_2$, $R_7$ and $R_8$, $R_5$ and $R_6$ may be linked together to form 1, 2, 3 or 4 carbocyclic or N, O and/or S-heterocyclic rings, which may be further fused with other aromatic rings and each N in a N-heterocyclic ring may be unsubstituted or substituted by $R_{10}$;
  and each alkyl, alkenyl, alkynyl, cycloalkyl or cycloalkylene group may be unsubstituted or substituted by one or more $R_{11}$;
  and each aryl, heteroaryl, aralkyl, arylene, heteroarylene or aralkylene may be unsubstituted or substituted by one or more $R_{12}$;
- $R_{10}$ is $R_{13}$; $COR_{13}$, $COOR_{13}$; or $CONR_{13}R_{14}$;
- $R_{11}$ is halogen, OH; $NR_{15}R_{16}$; O—$R_{15}$; S—$R_{15}$; O—CO—$R_{15}$; CO—$R_{15}$; oxo; thiono; CN; $COOR_{15}$; $CONR_{15}R_{16}$; $SO_2NR_{15}R_{16}$; $SO_2R_{15}$; $SO_3R_{15}$; $SiR_{15}R_{16}R_{17}$; $OSiR_{15}R_{16}R_{17}$; $POR_{15}R_{16}$; or a radical —X-Sil;
- $R_{12}$ is $C_1$-$C_{12}$alkylthio; $C_3$-$C_{12}$cycloalkylthio; $C_1$-$C_{12}$alkenylthio; $C_3$-$C_{12}$cycloalkenylthio; $C_1$-$C_{12}$alkoxy; $C_3$-$C_{12}$cycloalkoxy; $C_1$-$C_{12}$alkenyloxy; or $C_3$-$C_{12}$cycloalkenyloxy which may be unsubstituted or substituted by one or more $R_{11}$; halogen; CN; SH; OH; CHO; $R_{18}$; $OR_{18}$; $SR_{18}$; $C(R_{18})$=$CR_{19}R_{20}$; O—CO—$R_{19}$; $NR_{18}R_{19}$; $CONR_{18}R_{19}$; $SO_2NR_{18}R_{19}$; $SO_2R_{18}$; $COOR_{18}$; $OCOOR_{18}$; $NR_{18}COR_{19}$; $NR_{19}COOR_{20}$; $SiR_{15}R_{16}R_{17}$; $OSiR_{15}R_{16}R_{17}$; P(=O)$R_{19}R_{20}$; or a radical —X-Sil;

- $R_{13}$, $R_{14}$, $R_{15}$, $R_{16}$, $R_{17}$, $R_{18}$, $R_{19}$ and $R_{20}$ independently of each other are hydrogen; $C_1$-$C_{22}$alkyl; $C_3$-$C_{12}$cycloalkyl; $C_2$-$C_{12}$alkenyl; $C_3$-$C_{12}$cycloalkenyl; $C_6$-$C_{14}$aryl; $C_4$-$C_{12}$heteroaryl; $C_7$-$C_{18}$aralkyl; or $C_5$-$C_{16}$heteroaralkyl; or
- $R_{13}$ and $R_{14}$, $R_{15}$ and $R_{16}$, $R_{16}$ and $R_{17}$ and/or $R_{18}$ and $R_{19}$ may be linked together to form unsubstituted or $C_1$-$C_4$alkyl-substituted pyrrolidine, piperidine, piperazine or morpholine;
- X is a linker; and
- Sil is a silane-, oligosiloxane or polysiloxane moiety;
- t is a number from 0 to 12;
- u is a number from 1 to 12;
- v is a number from 0 to 12;
- if n=1
- $R_1$ and $R_2$ independently of each other hydrogen; $C_1$-$C_{22}$ alkyl; hydroxy-$C_1$-$C_{22}$alkyl; $C_2$-$C_{22}$alkenyl; $C_2$-$C_{22}$ alkynyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_6$-$C_{20}$aryl; $C_5$-$C_{11}$heteroaralkyl; $C_4$-$C_9$heteroaryl; or a radical of formula

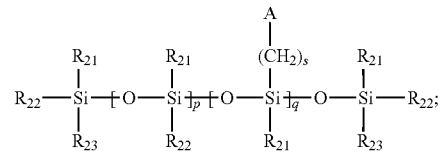

- $R_{21}$, $R_{22}$, $R_{23}$ independently from each other are $C_1$-$C_{22}$alkyl; or $C_1$-$C_{22}$alkoxy;
- a is the bond to the linker X;
- $R_3$ is CN; $NR_5R_6$; —$COR_5$; —$COOR_5$; —$SO_2R_5$; —$CONR_5R_6$; $C_6$-$C_{20}$aryl; or $C_4$-$C_9$heteroaryl;
- p is a number from 0 to 100
- q is a number from 1 to 20;
- s is a number from 0 to 4;
- if n=2
- $R_1$ and $R_2$ are each a bivalent radical selected from $C_1$-$C_5$alkylene which may be interrupted by one or more oxygen atoms; or
- $R_1$ and $R_2$ together with the nitrogen atoms form a six-membered heterocyclic ring; and simultaneously $R_3$ is defined as for n=1; or
- $R_3$ is a bivalent radical of formula —CO—$V_1$—$C_1$-$C_{12}$alkylene-$W_1$—*, wherein
- the asterix indicates the bond to the second $R_3$
- $V_1$ is —O—; or —$NR_7$—; or the direct bond;
- $W_1$ is the linkage to the second $R_3$, wherein $W_1$ is the direct bond; or selected from $C_1$-$C_{12}$alkylene; or phenylene; and
- $R_1$ and $R_2$ simultaneously are defined as for n=1;
- if n=3
- one of $R_1$, $R_2$ or $R_3$ is a trivalent radical;

if n=4
R$_1$ or R$_2$ is a radical of formula

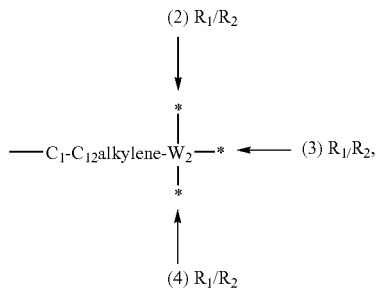

wherein
the asterices indicate the bond to the second, third and fourth R$_1$/R$_2$;
W$_2$ is

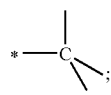

R$_3$ is defined as for n=1; or
R$_3$ is a radical of formula

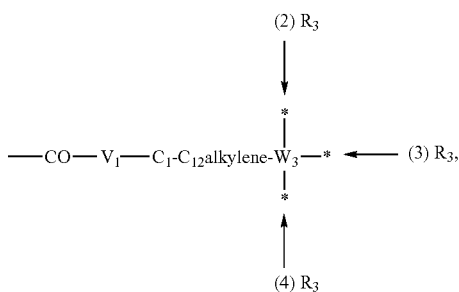

wherein the asterices indicate the bond to the second (2), third (3) and fourth (4) R$_3$; and
W$_3$ is

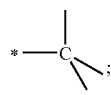

or
R$_1$ or R$_2$ is a radical of formula

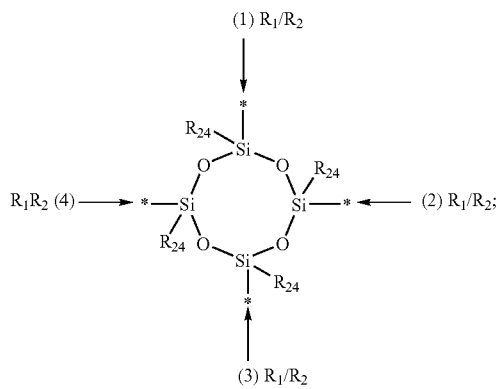

the asterices indicate the bond to the second, third and fourth R$_1$/R$_2$;
R$_{24}$ is C$_1$-C$_{22}$alkyl; or C$_1$-C$_{22}$alkoxy
and
pigments, lakes or soluble dyes.

2. A method according to claim 1, wherein
L$_1$, L$_2$ or L$_3$, independently from each other are hydrogen; hydroxy; C$_1$-C$_5$alkyl, which may be interrupted by one or more oxygen; COOR$_9$; phenyl, which may be substituted by one or more halogen, C$_1$-C$_5$alkyl, C$_1$-C$_5$alkoxy, trifluoroalkyl, C$_2$-C$_5$alkenyl; C$_4$-C$_9$heteroaryl; and
R$_9$ is defined as in claim 1; and
n is 1.

3. A method according to claim 1, wherein
L$_1$, L$_2$ and L$_3$, independently from each other are hydrogen, methyl, phenyl; or —COOR$_9$; wherein
R$_9$ is C$_1$-C$_5$alkyl; and
n is 1.

4. A method according to claim 1, wherein L$_1$ and L$_3$ together form a bivalent radical selected from the group consisting of

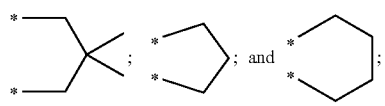

R$_4$ is CN;
R$_3$ is —COOR$_5$;
R$_5$ is C$_1$-C$_{22}$alkyl;
R$_1$ is hydrogen and R$_2$ is C$_1$-C$_{22}$ alkyl.

5. A method according to claim 1, wherein
R$_1$ and R$_2$ independently from each other are C$_1$-C$_{12}$alkyl; hydroxy-C$_1$-C$_{12}$alkyl; phenyl or phenyl-C$_1$-C$_5$alkyl, which may be substituted by one or more C$_1$-C$_5$alkyl, or SO$_3$M; or a radical of formula

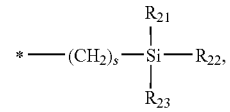

wherein
n is 1; and
R$_{21}$, R$_{22}$, R$_{23}$ and s are defined as in claim 1.

6. A method according to claim 5, wherein
R$_1$ and R$_2$, independently from each other are C$_1$-C$_4$alkyl; and
n is 1.

7. A method according to claim 1, wherein
R$_1$ and R$_2$ together form a bivalent radical selected from the group consisting of;

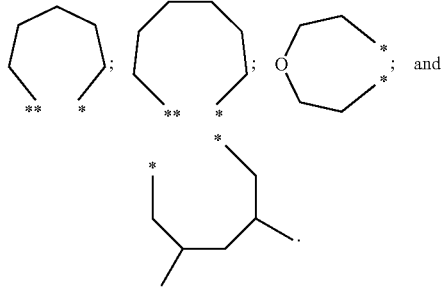

8. A method according to claim 1, wherein
R$_3$ is CN; —COR$_5$; —COOR$_5$; —SO$_2$R$_5$; or —CONR$_5$R$_6$;
R$_4$, is CN; —COR$_7$; —COOR$_7$; —CONR$_7$R$_8$; or —SO$_2$R$_7$; wherein
R$_5$, R$_6$, R$_7$ and R$_8$, independently from each other are C$_1$-C$_{22}$alkyl; phenyl; or a radical —X-Sil;
n is 1; and
X and Sil are defined as in claim 1.

9. A method according to claim 1, wherein $R_3$ and $R_4$ together form a carbyclic or heterocyclic biradical selected from the group consisting of

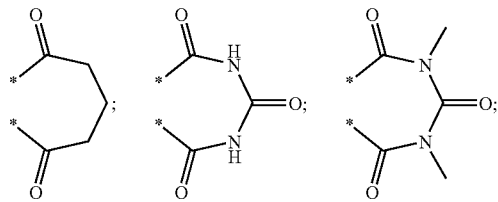

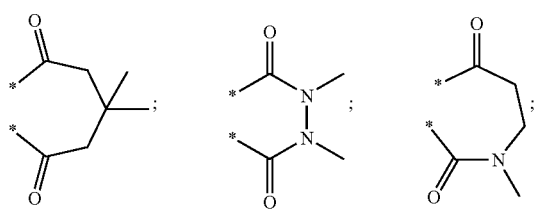

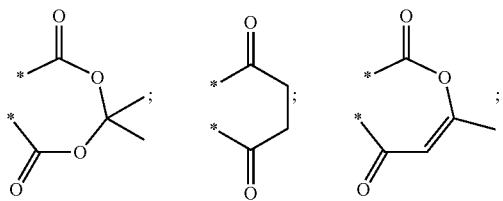

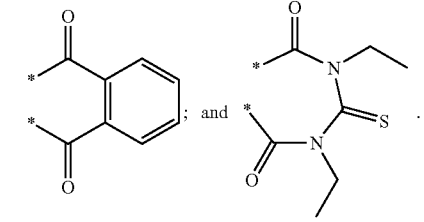

10. A method according to claim 1, wherein $R_2$ and $L_3$ form a bivalent radical selected from the group consisting of

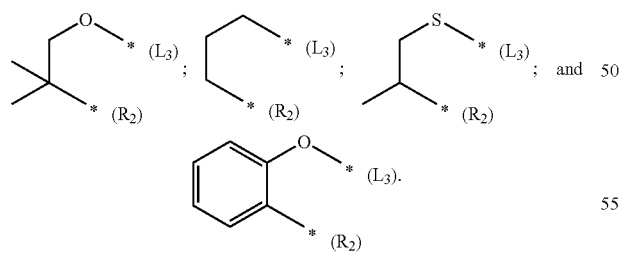

11. A method according to claim 1, wherein $L_1$, $L_2$ or $L_3$, independently from each other are hydrogen; hydroxy; $C_1$-$C_5$alkyl, which may be interrupted by one or more oxygen; $COOR_9$; phenyl, which may be substituted by one or more halogen, $C_1$-$C_5$alkyl, $C_1$-$C_5$alkoxy, trifluoroalkyl, $C_2$-$C_5$alkenyl; $C_4$-$C_9$heteroaryl; or $L_1$ and $L_2$ or $L_1$ and $L_3$ or $L_2$ and $L_3$ together form a bivalent radical selected from the group consisting of

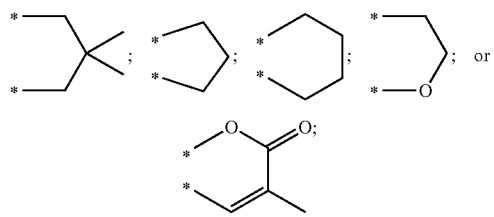

$R_1$ and $R_2$ independently from each other are $C_1$-$C_{12}$alkyl; hydroxy-$C_1$-$C_{12}$alkyl; phenyl or phenyl-$C_1$-$C_5$alkyl, which may be substituted by one or more $C_1$-$C_5$alkyl, or $SO_3M$; or a radical of formula

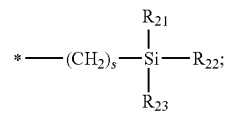

or $R_1$ and $R_2$ together form a bivalent radical selected from the group consisting of

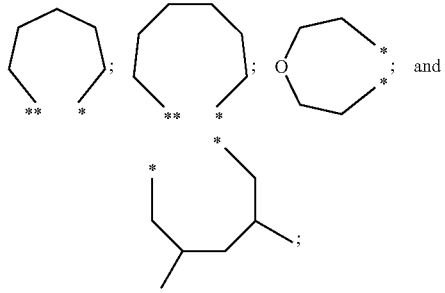

$R_3$ is CN; $COR_5$; $COOR_5$; $CONR_5R_8$; or $SO_2R_5$;

$R_4$ is CN; $COR_7$; $COOR_7$; $CONR_7R_8$; or $SO_2R_7$;

$R_7$, $R_5$ and $R_8$, independently from each other are $C_1$-$C_{22}$alkyl; phenyl; or a radical —X-Sil; or $R_3$ and $R_4$ together form a carbocyclic or heterocyclic biradical selected from the group consisting of

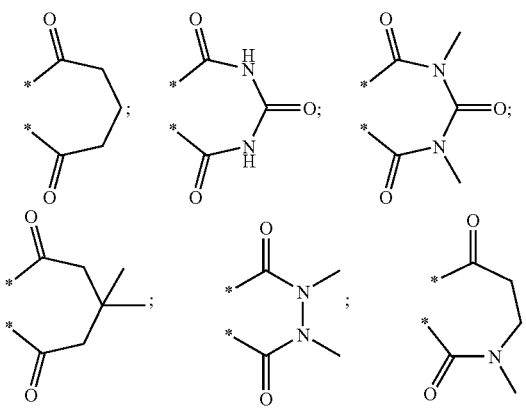

-continued

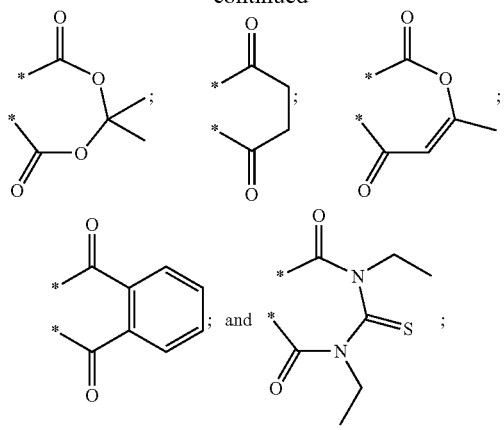

or $R_2$ and $L_3$ form a bivalent radical selected from the group consisting o

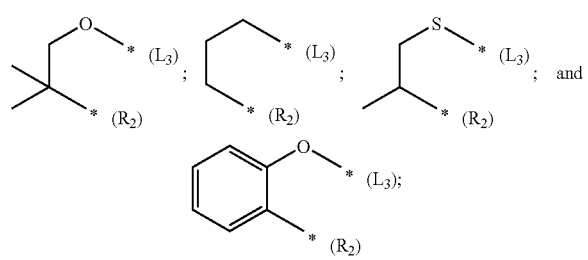

and $R_9$, $R_{21}$, $R_{22}$, $R_{23}$, X and Sil are defined as in claim 1.

12. A method according to claim 1, wherein the stabilizers correspond to formula

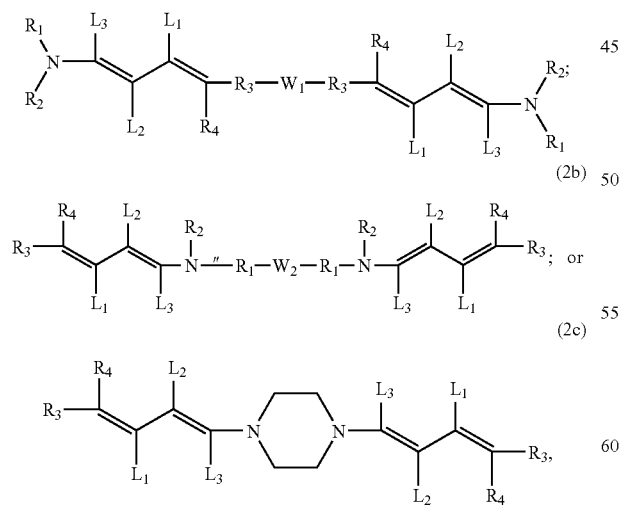

wherein $R_1$, $R_2$, $R_3$, $R_4$, $L_1$, $L_2$, $L_3$ $W_1$ and $W_2$ are defined as in claim 1.

13. A method according to claim 12, wherein in formula (2a)

$R_3$ is a radical of formula —CO—$V_1$—$C_1$-$C_{12}$alkylene-\*\*, wherein $V_1$ is —O; or —NH—;

$W_1$ is the direct bond; $C_1$-$C_4$alkylene; or phenylene;

$R_1$ and $R_2$, independently from each other are $C_1$-$C_{12}$alkyl;

$L_1$, $L_2$ and $L_3$ independently form each other are hydrogen; or $C_1$-$C_5$alkyl; or $L_3$ and $R_2$ together form a heterocyclic ring;

$R_4$ is CN; $COR_7$; $COOR_7$; $CONR_7R_8$; or $SO_2R_7$; and $R_7$ is $C_1$-$C_{22}$alkyl; or phenyl.

14. A method according to claim 12, wherein in formula (2b)

$R_1$ is $C_1$-$C_3$alkylene;

$L_1$, $L_2$ and $L_3$ independently from each other are hydrogen; or $C_1$-$C_5$alkyl; or $L_1$ and $L_3$ together form a carbocyclic ring;

$R_2$ is hydrogen; or $C_1$-$C_5$alkyl;

$W_1$ is $C_1$-$C_3$alkylene; or the direct bond;

$R_3$ and $R_4$ independently from each other are CN; $COR_7$; $COOR_7$; $CONR_7R_8$; or $SO_2R_7$; and $R_7$ and $R_8$, independently from each other are $C_1$-$C_{22}$alkyl; or phenyl.

15. A method according to claim 1, wherein the stabilizers correspond to the formula

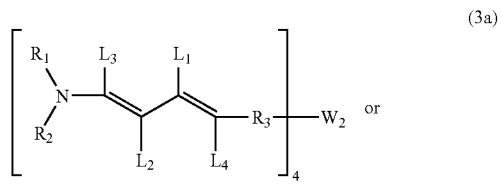

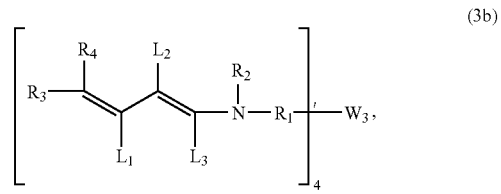

wherein $R_1$, $R_2$, $R_3$, $R_4$, $L_1$, $L_2$, $L_3$, $W_2$ and $W_3$ are defined as in claim 1.

16. A method according to claim 15, wherein in formula (3a)

$L_1$, $L_2$ and $L_3$ independently from each other are hydrogen; hydroxy; $C_1$-$C_5$alkyl; or $L_1$ and $L_3$ together form a carbocyclic ring;

$R_1$ and $R_2$ independently from each other are hydrogen; or $C_1$-$C_{12}$alkyl;

$R_3$ is \*—CO—$V_1$—$C_1$-$C_{12}$alkylene-\*\*;

$V_1$ is —O—; or —NH—;

W is a tetravalent radical of formula

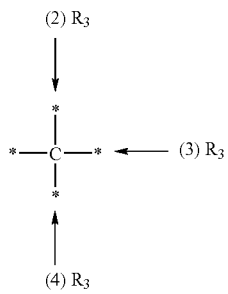

$R_4$ is CN; $COR_7$; $COOR_7$; $CONR_7R_8$; or $SO_2R_7$; and $R_7$ and $R_8$, independently from each other are $C_1$-$C_{22}$alkyl; or phenyl.

17. A method according to claim 1 wherein the body-care products are for the skin and its adnexa.

18. A method according to claim 17, wherein the body-care products are selected from the group consisting of skin-care products, bath and shower additives, preparations containing fragrances and odoriferous substances, hair-care products, dentifrices, deodorizing and antiperspirant preparations, decorative preparations, light protection formulations and preparations containing active ingredients.

19. A method according to claim 17, wherein the body-care products are selected from the group consisting of body oils, body lotions, body gels, treatment creams, skin protection ointments, shaving preparations and skin powders.

20. A method according to claim 18, wherein the preparations contain fragrances and odoriferous substances which are selected from the group consisting of scents, perfumes, toilet waters and shaving lotions.

21. A method according to claim 18, wherein the hair-care products are selected from the group consisting of shampoos, hair conditioners, products for styling and treating hair, perming agents, hair sprays and lacquers, hair gels, hair fixatives and hair dyeing or bleaching agents.

22. A method according to claim 18, wherein the decorative preparations are selected from the group consisting of lipsticks, nail varnishes, eye shadows, mascaras, dry and moist make-up, rouge, powders, depilatory agents and suntan lotions.

23. A method according to claim 18, wherein the body-care products contain active ingredients and are selected from the group consisting of hormone preparations, vitamin preparations, vegetable extract preparations and antibacterial preparations.

24. A method according to claim 1 wherein the household products are selected from the group consisting of household cleaning and treating agents.

25. A method according to claim 24 wherein the household cleaning and treating agents are selected from the group consisting of washing, rinsing and dishwashing agents, shoe polishes, polishing waxes, floor detergents and polishes, all purpose cleaners, bath and toilet cleaners, kitchen cleaners, car shampoos and waxes, neutral, acidic and alkaline cleaners, metal, glass and ceramic cleaners, textile care agents, agents for removing rust, color and stains, bleaches, furniture and multipurpose polishes, surface protecting formulations, film forming formulations, air care formulations and candles.

26. A body-care or household product wherein said body-care and household products are stored in a container and said container has a low absorption in the UV-A range comprising about 5 to about 10000 ppm of compounds of formula

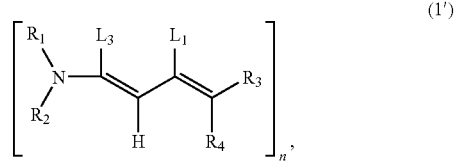

wherein $R_3$ is CN; $NR_5R_6$; —$COR_5$; —$COOR_5$; —$SO_2R_5$; —$CONR_5R_6$; $C_6$-$C_{20}$aryl; or $C_4$-$C_9$heteroaryl;

$R_4$ is CN; —$COR_7$; —$COOR_7$; —$CONR_7R_8$; $C_1$-$C_{22}$alkyl; $C_2$-$C_{22}$alkenyl; $C_2$-$C_{22}$ alkynyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_5$-$C_{11}$heteroaralkyl; $C_6$-$C_{20}$ aryl; $C_1$-$C_1$alkylcarbonylamino-$C_6$-$C_{20}$aryl; or $C_4$-$C_9$heteroaryl;

$R_5$, $R_6$, $R_7$ and $R_8$ are independently of each other hydrogen; $C_1$-$C_{22}$alkyl, $C_2$-$C_{22}$alkenyl, $C_2$-$C_{22}$alkynyl; $C_3$-$C_{12}$cycloalkyl; $C_3$-$C_{12}$cycloalkenyl; $C_7$-$C_{20}$ aralkyl; $COR_9$, —(CO)—COO—$R_9$, $C_1$-$C_{20}$heteroalkyl; $C_3$-$C_{12}$cycloheteroalkyl; $C_5$-$C_{11}$heteroaralkyl; $C_6$-$C_{20}$ aryl; $C_1$-$C_5$alkoxy-$C_6$-$C_{20}$aryl; —(CH$_2$)$_t$—SO$_3$H; —(CH$_2$)$_t$—(CO)—OR$_9$; —(CH$_2$)$_t$—O—C$_6$-C$_{10}$aryl; —(CH$_2$)$_v$COO—R$_9$; $C_4$-$C_9$heteroaryl; —(CH$_2$)$_u$—SiR$_{15}$R$_{16}$R$_{17}$; or a radical —X-Sil;

$R_9$ is hydrogen; $C_1$-$C_{22}$alkyl; $C_2$-$C_{22}$alkenyl; $C_2$-$C_{22}$alkynyl; $C_3$-$C_{12}$cycloalkyl; $C_3$-$C_{12}$cycloalkenyl; $C_7$-$C_{20}$ aralkyl; $C_1$-$C_{20}$heteroalkyl; $C_3$-$C_{12}$cycloheteroalkyl; $C_5$-$C_{11}$heteroaralkyl; $C_6$-$C_{20}$aryl; or $C_4$-$C_9$heteroaryl; or $L_1$ and $L_3$, are H or may be linked together to form 1, 2, 3 or 4 carbocyclic or N, O and/or S-heterocyclic rings, which may be further fused with other aromatic rings and each N in a N-heterocyclic ring may be unsubstituted or substituted by $R_{10}$;

and each alkyl, alkenyl, alkynyl, cycloalkyl or cycloalkylene group may be unsubstituted or substituted by one or more $R_{11}$;

and each aryl, heteroaryl, aralkyl, arylene, heteroarylene or aralkylene may be unsubstituted or substituted by one or more $R_{12}$;

$R_{10}$ is $R_{13}$; $COR_{13}$, $COOR_{13}$; or $CONR_{13}R_{14}$;

$R_{11}$ is halogen, OH; $NR_{15}R_{16}$; O—$R_{15}$; S—$R_{15}$; CO—$R_{15}$; oxo; thiono; CN; $COOR_{15}$; $CONR_{15}R_{16}$; $SO_2NR_{15}R_{16}$; $SO_2R_{15}$; $SO_3R_{15}$; $SiR_{15}R_{16}R_{17}$; $OSiR_{15}R_{16}R_{17}$; $POR_{15}R_{16}$; or a radical —X-Sil;

$R_{12}$ is $C_1$-$C_{12}$alkylthio; $C_3$-$C_{12}$cycloalkylthio; $C_1$-$C_{12}$alkenylthio; $C_3$-$C_{12}$cycloalkenylthio; $C_1$-$C_{12}$alkoxy; $C_3$-$C_{12}$cycloalkoxy; $C_1$-$C_{12}$alkenyloxy; or $C_3$-$C_{12}$cycloalkenyloxy which may be unsubstituted or substituted by one or more $R_{11}$; halogen; CN; SH; OH; CHO; $R_{18}$; $OR_{18}$; $SR_{18}$; $C(R_{18})$=$CR_{19}R_{20}$; O—CO—$R_{19}$; $NR_{18}R_{19}$; $CONR_{18}R_{19}$, $SO_2NR_{18}R_{19}$, $SO_2R_{18}$, $COOR_{18}$, $OCOOR_{18}$; $NR_{18}COR_{19}$, $NR_{19}COOR_{20}$; $SiR_{15}R_{16}R_{17}$; $OSiR_{15}R_{16}R_{17}$; P(=O)$R_{19}R_{20}$; or a radical —X-Sil;

$R_{13}$, $R_{14}$, $R_{15}$, $R_{16}$, $R_{17}$, $R_{18}$, $R_{19}$ and $R_{20}$ independently of each other are hydrogen; $C_1$-$C_{22}$alkyl; $C_3$-$C_{12}$cycloalkyl; $C_2$-$C_{12}$alkenyl; $C_3$-$C_{12}$cycloalkenyl; $C_6$-$C_{14}$aryl; $C_4$-$C_{12}$heteroaryl; $C_7$-$C_{18}$aralkyl; or $C_5$-$C_{16}$heteroaralkyl; or $R_{13}$ and $R_{14}$, $R_{15}$ and $R_{16}$, $R_{16}$ and $R_{17}$ and/or $R_{18}$ and $R_{19}$ may be linked together to form unsubstituted or $C_1$-$C_4$alkyl-substituted pyrrolidine, piperidine, piperazine or morpholine;

X is a linker; and
Sil is a silane-, oligosiloxane or polysiloxane moiety;
t is a number from 0 to 12;
u is a number from 1 to 12;
v is a number from 0 to 12;
if n=1
$R_1$ and $R_2$ independently of each other hydrogen; $C_1$-$C_{22}$alkyl; hydroxy-$C_1$-$C_{22}$alkyl; $C_2$-$C_{22}$alkenyl; $C_2$-$C_{22}$alkynyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_6$-$C_{20}$aryl; $C_5$-$C_{11}$heteroaralkyl; $C_4$-$C_9$heteroaryl; or a radical of formula

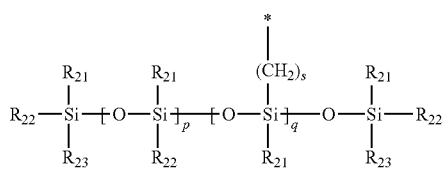

$R_{21}$, $R_{22}$, $R_{23}$ independently from each other are $C_1$-$C_{22}$alkyl; or $C_1$-$C_{22}$alkoxy;
p is a number from 0 to 100
q is a number from 1 to 20;
s is a number from 0 to 4;
$R_3$ is CN; $NR_5R_6$; —$COR_5$; —$COOR_5$; —$SO_2R_5$; —$CONR_5R_6$; $C_6$-$C_{20}$aryl; or $C_4$-$C_9$heteroaryl;
if n=2
$R_1$ and $R_2$ are each a bivalent radical selected from $C_1$-$C_5$alkylene which may be interrupted by one or more oxygen atoms; or
$R_1$ and $R_2$ together with the nitrogen atoms form a six-membered heterocyclic ring; and simultaneously $R_3$ is defined as for n=1; or
$R_3$ is a bivalent radical of formula —CO—$V_1$—$C_1$-$C_{12}$alkylene-$W_1$—*, wherein
the asterix indicates the bond to the second $R_3$
$V_1$ is —O—; or —$NR_7$—; or the direct bond;
$W_1$ is the linkage to the second $R_3$, wherein $W_1$ is the direct bond; or selected from $C_1$-$C_{12}$alkylene; or phenylene; and
$R_1$ and $R_2$ simultaneously are defined as for n=1;
if n=3
one of $R_1$, $R_2$ or $R_3$ is a trivalent radical;
if n=4
$R_1$ or $R_2$ is a radical of formula

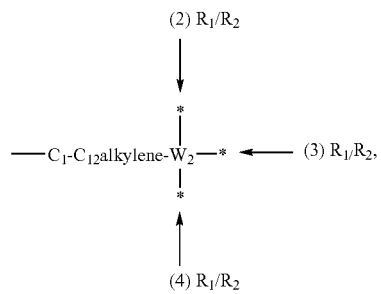

wherein
the asterices indicate the bond to the second, third and fourth $R_1/R_2$;

$W_2$ is

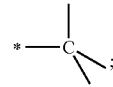

$R_3$ is defined as for n=1; or
$R_3$ is a radical of formula

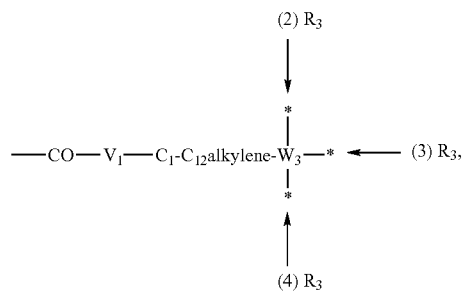

wherein the asterices indicate the bond to the second (2), third (3) and fourth (4) $R_3$; and
$W_3$ is

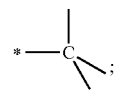

or
$R_1$ or $R_2$ is a radical of formula

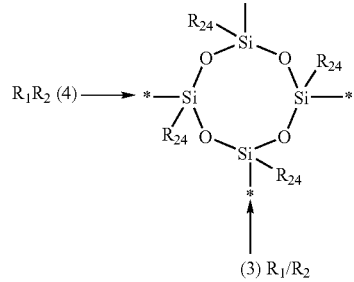

the asterices indicate the bond to the second, third and fourth $R_1/R_2$;
$R_{24}$ is $C_1$-$C_{22}$alkyl; or $C_1$-$C_{22}$alkoxy;
wherein at least one of the radicals $R_1$, $R_2$, $R_3$ or $R_4$ is a silicon organic compound.

27. The method according to claim 1, wherein the body-care products are selected from the group consisting of skin-care products, bath and shower additives, preparations containing fragrances and odoriferous substances, hair-care products, dentifrices, deodorizing and antiperspirant preparations, decorative preparations, light protection formulations and preparations containing active ingredients and the household products are a household cleaning product and the household cleaning product are selected from the group consisting of washing, rinsing and dishwashing agents, floor detergents and polishes, all purpose cleaners, bath and toilet cleaners, kitchen cleaners, car shampoos, neutral, acidic and alkaline cleaners, metal, glass and ceramic cleaners and agents for removing rust, color and stains, bleaches.

* * * * *